US007638607B2

(12) United States Patent
Vale, Jr. et al.

(10) Patent No.: US 7,638,607 B2
(45) Date of Patent: *Dec. 29, 2009

(54) UROCORTIN PROTEINS AND USES THEREOF

(75) Inventors: Wylie Walker Vale, Jr., La Jolla, CA (US); Teresa M Reyes, Encinitas, CA (US); Paul E Sawchenko, Carlsbad, CA (US); Jean E F Rivier, La Jolla, CA (US); Kathy A Lewis, San Diego, CA (US); John B Hogenesch, Encinitas, CA (US); Joan M Vaughan, San Diego, CA (US); Marilyn H Perrin, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/784,317

(22) Filed: Apr. 5, 2007

(65) Prior Publication Data

US 2007/0191592 A1    Aug. 16, 2007

Related U.S. Application Data

(60) Continuation of application No. 10/973,092, filed on Oct. 25, 2004, now Pat. No. 7,223,846, which is a division of application No. 09/919,473, filed on Jul. 31, 2001, now Pat. No. 6,838,274.

(60) Provisional application No. 60/223,255, filed on Aug. 4, 2000, provisional application No. 60/273,969, filed on Mar. 7, 2001.

(51) Int. Cl.
*A61K 38/27* (2006.01)
*A61K 38/00* (2006.01)
*A01N 37/18* (2006.01)
*C07K 1/00* (2006.01)
*C07K 14/00* (2006.01)

(52) U.S. Cl. .................. 530/399; 530/350; 530/300; 530/332; 530/402; 514/2; 514/12

(58) Field of Classification Search .......... None
See application file for complete search history.

(56) References Cited

U.S. PATENT DOCUMENTS

2002/0082409 A1   6/2002  Hsu ........................ 536/23.5
2003/0165807 A1   9/2003  Isfort et al. .................. 435/4

FOREIGN PATENT DOCUMENTS

WO    WO 97/00063    1/1997
WO    WO 02/34934    5/2002

OTHER PUBLICATIONS

Hsu and Hsueh, "Human stresscopin and stresscopin-related peptide are selective ligands for the type 2 corticotropin-releasing hormone receptor," *Nature Medicine* 7: 605-611, May 2001.

Lewis, K. et al., "Identificiation of urocortin III, an additional member of the corticotropin-releasing factor (CRF) family with high affinity for the CRF2 receptor," *Proc. Natl. Acad. Sci. USA* 98(13): 7570-7575, Jun. 19, 2001.

Reyes, T.M. et al., "Urocortin II: A member of the corticotropin-releasing factor (CRF) neuropeptide family that is selectively bound by type 2 CRF receptors," *Proc. Natl. Acad. Sci. USA* 98(5): 2843-2848, Feb. 27, 2001.

GenBank Database, Accession No. AC005903, Jan. 9, 2003.
GenBank Database, Accession No. AF331517, Mar. 6, 2001.
GenBank Database, Accession No. BE622276, Oct. 20, 2000.

Hsu et al., "Stresscopins and Their Uses," U.S. Appl. No. 60/244,128, filed Oct. 26, 2000.

Hsu et al., "Stresscopins and Their Uses," U.S. Appl. No. 60/276,615, filed Mar. 15, 2001.

Bale et al., "Mice deficient for corticotrophin-releasing hormone receptor-2 display anxiety-like behaviour and are hypersensitive to stress," *nature genetics* 24:410-414, Apr. 2000.

Bittencourt et al., "Do Centrally Administered Neuropeptides Access Cognate Receptors?: An Analysis in the Central Corticotropin-Releasing Factor System," *The Journal of Neuroscience* 20(3):1142-1156, Feb. 2000.

Bradbury et al., "Modulation of Urocortin-Induced Hypophagia and Weight Loss by Corticotropin-Releasing Factor Receptor 1 Deficiency in Mice," *Endocrinology* 141(8):2715-2724, 2000.

Chalmers et al., "Localization of Novel Corticotropin-Releasing Factor Receptor ($CRF_2$) mRNA Expression to Specific Subcortical Nuclei in Rat Brain: Comparison with $CRF_1$ Receptor mRNA Expression," *The Journal of Neuroscience* 15(10):6340-6350, Oct. 1995.

Chen et al., "Expression cloning of a human corticotrophin-releasing-factor receptor," *Proc. Natl. Acad. Sci. USA* 90:8967-8971, Oct. 1993.

(Continued)

*Primary Examiner*—Olga N Chernyshev
(74) *Attorney, Agent, or Firm*—Seed IP Law Group PLLC

(57) ABSTRACT

A human urocortin-related peptide with significant sequence homology to the CRF neuropeptide family was identified. A mouse CDNA was isolated from whole brain poly (A+) RNA that encodes a predicted 38 amino acid peptide protein designated herein as urocortin II. Both human URP and mouse Ucn II are structurally related to the other known mammalian family members, CRF and urocortin (Ucn). These peptides are involved in the regulation of the hypothalamic-pituitary-adrenal axis under basal and stress conditions, suggesting a similar role for URP and Ucn IL Synthesized Ucn-II and URP peptide binds with higher affinity to CRF-R2 than to CRF-R1 Ucn II and human URP appear to be involved in the regulation of body temperature and appetite and may play a role in other stress related phenomenon. These findings identify Ucn II and human URP as a new members of the CRF family of neuropeptides, which are expressed centrally and bind to CRF-R2.

4 Claims, 19 Drawing Sheets

OTHER PUBLICATIONS

Contarino et al., "Dissociation of locomotor activation and suppression of food intake induced by CRF in CRFR1-deficient mice," *Endocrinology* 141(7):2698-2702, 2000.

Coste et al., "Abnormal adaptations to stress and impaired cardiovascular function in mice lacking corticotropin-releasing hormone receptor-2," *nature genetics* 24:403-409, Apr. 2000.

Eddy, Sean R., "Hidden Markov models," *Current Opinion in Structural Biology* 6:361-365, 1996.

Elmquist et al., "Unraveling the central nervous system pathways underlying responses to leptin," *nature neuroscience* 1(6):445-450, Oct. 1998.

Gray et al., "Identification of a Binding Site on the Type II Activin Receptor for Activin and Inhibin," *The Journal of Biological Chemistry* 275(5):3206-3212, Feb. 2000.

Kishimoto et al., "Deletion of *Crhr2* reveals an anxiolytic role for corticotrophin-releasing hormone receptor-2," *nature genetics* 24:415-419, Apr. 2000.

Lovenberg et al., "$CRF_{2\alpha}$ and $CRF_{2\beta}$ receptor mRNAs are differentially distributed between the rat central nervous system and peripheral tissues." *Endocrinology* 136(9):4139-4142, 1995.

Miranda et al., "Conformationally Restricted Competitive Antagonists of Human/Rat Corticotropin-Releasing Factor," *J. Med. Chem.* 37:1450-1459, 1994.

Perrin et al., "Identification of a second corticotrophin-releasing factor receptor gene and characterization of a cDNA expressed in heart," *Proc. Natl. Acad. Sci. USA* 92:2969-2973, Mar. 1995.

Potter et al., "Distribution of corticotrophin-releasing factor receptor mRNA expression in the rat brain and pituitary," *Proc. Natl. Acad. Sci. USA* 91:8777-8781, Sep. 1994.

Rohde et al., "Corticotropin-Releasing Hormone (CRH) Receptors in the Mesenteric Small Arteries of Rats Resemble the (2)-Subtype," *Biochemical Pharmacology* 52:829-833, 1996.

Smith et al., "Corticotropin Releasing Factor Receptor 1-Deficient Mice Display Decreased Anxiety, Impaired Stress Response, and Aberrant Neuroendocrine Development," *Neuron* 20:1093-1102, Jun. 1998.

```
CTC ACG ATG ACC AGG TGT GCT CTG CTG TTG CTG ATG GTC CTG ATG TTG GGC AGA GTC CTG
     M   T   R   C   A   L   L   L   L   M   V   L   M   L   G   R   V   L
     1                              10                                            
GTT GTC CCA GTG ACC CCT ATC ACC TTC CAG CTC CGC CCT CAG AAT TCT CCC CAG ACC
 V   V   P   V   T   P   I   T   F   Q   L   R   P   Q   N   S   P   Q   T
        20                              30
ACT CCC CGA CCT GCG GCC TCA GAG AGC CCC TCA GCT GCT CCC ACA TGG CCG TGG GCT GCC
 T   P   R   P   A   A   S   E   S   P   S   A   A   P   T   W   P   W   A   A
                    40                              50
CAG AGC CAC TGC AGC CCC ACC CGC CAC CCT GGC TCG CGC ATT GTC CTA TCG CTG GAT GTC
 Q   S   H   C   S   P   T   R   H   P   G   S   R   I   V   L   S   L   D   V
            60                              70
CCC ATC GGC CTC TTG CAG ATC TTA GAG CAA CTG GCC CGG GCC AGG GCT GCC AGG GAG CAG
 P   I   G   L   L   Q   I   L   E   Q   L   A   R   A   R   A   A   R   E   Q
        80                              90
GCC ACC AAC GCC CGC ATC CTG GCC CGT GTC GGC CAC TGC TGA GCC TGA GAG AGG GGG
 A   T   N   A   R   I   L   A   R   V   G   H   C   *            (SEQ ID NO:2)
                  100                             110

TCA CAG TGA TAG GGC CAC CCT GGA TGG GAA GAC CTG GAG    (SEQ ID NO: 1)
```

FIG. 1

CTC ACG ATG ACC AGG TGT GCT CTG CTG TTG CTG ATG GTC CTG ATG TTG GGC AGA GTC CTG
         M   T   R   C   A   L   L   L   L   M   V   L   M   L   G   R   V   L

GTT GTC CCA GTG ACC CCT ATC CCA ACC TTC CAG CTC CGC CCT CAG AAT TCT CCC CAG ACC
 V   V   P   V   T   P   I   P   T   F   Q   L   R   P   Q   N   S   P   Q   T

ACT CCC CGA CCT GCG GCC TCA GAG AGC CCC TCA GCT GCT CCC ACA TGG CCG TGG GCT GCC
 T   P   R   P   A   A   S   E   S   P   S   A   A   P   T   W   P   W   A   A

CAG AGC CAC TGC AGC CCC ACC CGC CAC CCT GGC TCG CGG ATT GTC CTA TCG CTG GAT GTC
 Q   S   H   C   S   P   T   R   H   P   G   S   R   I   V   L   S   L   D   V

CCC ATC GGC CTC TTG CAG ATC TTA CTG GAG CAA CTG GCC CGG GCC AGG GCT GCC AGG GAG CAG
 P   I   G   L   L   Q   I   L   L   E   Q   L   A   R   A   R   A   A   R   E   Q

GCC ACC AAC GCC ATC CTG GCC CGT GTC GGC CAC TGC TGA GCC TGA GAG AGG GGG
 A   T   N   A   R   I   L   A   R   V   G   H   C   *        (SEQ ID NO:2)

TCA CAG TGA TAG GGC CAC CCT GGA TGG GAA GAC CTG GAG     (SEQ ID NO:1)

FIG. 2

| | | | | |
|---|---|---|---|---|
| hURP | XVLSLDVPIGLLQLLLEQARARAREQATTMNARTLARV | 38/38 | (SEQ ID NO: 4) |
| hUcn | DNPSLSIDLTFHLLRTLLELARTQSQRERAEQNRIIFDSV | 16/38 | (SEQ ID NO: 5) |
| hCRF | SEEPPISLDLTFHLLREVLEMARAEQLAQQAHSNRKLMEII | 13/38 | (SEQ ID NO: 6) |
| cUro | NDDPPISIDLTFHLLRNMIEMARIENQREQAFLINRKYLDEV | 14/38 | (SEQ ID NO: 7) |
| fSvg | -EGPPISIDLSLELLRKMIEIEKQEKEKQAANMRLLLDTI | 10/38 | (SEQ ID NO: 8) |
| dCRF/Uro | PAETPNSLDLTFHLLREMIEIAKHENQQMQADSNRIMDTI | 12/38 | (SEQ ID NO: 9) |

FIG. 3

MTRWALVWFVVLMLDRILFVPGTPIPTFQLLPQNSLETTP 40
SSVTSESSSGTTTGPSASWSNSKASPYLDTRVILSLDVPI 80
GLLRILLEQARYKAARNQAATNAQILAHVGRR (SEQ ID NO: 10) 112

FIG. 4A mouse Ucn II: VILSLDVPIGLLRILLEQARYKAARNQAATNAQILAHV. (SEQ ID NO: 11)
human URP:   IVLSLDVPIGLLQLLLEQARARAQAATTQMARLARV. (SEQ ID NO: 04)
fish URP:    LTLSLDVPTNIMNVFDVAKAKNLRAKAAFMARLLAHI. (SEQ ID NO: 12)
rat Ucn:     DDPPLSIDLTFHLLRTLLELARTQSQREAEQNRIIFDSM. (SEQ ID NO: 13)
r/hCRF:      SEEPPISLDLTFHLLREVLEMARAEQLAQQAHSNRKLMEII. (SEQ ID NO: 06)

FIG. 4B

SEQUENCE LISTING

<160> NUMBER OF SEQ ID NOS: 13

<210> SEQ ID NO 1
<211> LENGTH: 399
<212> TYPE: DNA
<213> ORGANISM: Homo sapiens

<400> SEQUENCE: 1

```
ctcacgatga ccaggtgtgc tctgctgttg ctgatggtcc tgatgttggg cagagtcctg      60
gttgtcccag tgaccectat cccaaccttc cagctccgcc ctcagaattc tccccagacc     120
actccccgac ctgcggcctc agagagcccc tcagctgctc ccacatggcc gtgggctgcc     180
cagagccact gcagccccac ccgccaccct ggctcgcgca ttgtcctatc gctggatgtc     240
cccatcggcc tcttgcagat cttactggag caagcccggg ccagggctgc cagggagcag     300
gccaccacca acgcccgcat cctggcccgt gtcggccact gctgagcctg agagagggg      360 tcacagtgat agggccaccc tggatgggaa gacctggag                            399
```

<210> SEQ ID NO 2
<211> LENGTH: 112
<212> TYPE: PRT
<213> ORGANISM: Homo sapiens

<400> SEQUENCE: 2

```
Met Thr Arg Cys Ala Leu Leu Leu Leu Met Val Leu Met Leu Gly Arg
  1               5                  10                  15

Val Leu Val Val Pro Val Thr Pro Ile Pro Thr Phe Gln Leu Arg Pro
                 20                  25                  30

Gln Asn Ser Pro Gln Thr Thr Pro Arg Pro Ala Ala Ser Glu Ser Pro
             35                  40                  45

Ser Ala Ala Pro Thr Trp Pro Trp Ala Ala Gln Ser His Cys Ser Pro
         50                  55                  60

Thr Arg His Pro Gly Ser Arg Ile Val Leu Ser Leu Asp Val Pro Ile
 65                  70                  75                  80

Gly Leu Leu Gln Ile Leu Leu Glu Gln Ala Arg Ala Arg Ala Ala Arg
                 85                  90                  95

Glu Gln Ala Thr Thr Asn Ala Arg Ile Leu Ala Arg Val Gly His Cys
                100                 105                 110
```

<210> SEQ ID NO 3
<211> LENGTH: 41
<212> TYPE: PRT
<213> ORGANISM: Homo sapiens

```
<400> SEQUENCE: 3

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Gly His Cys
        35                  40

<210> SEQ ID NO 4
<211> LENGTH: 38
<212> TYPE: PRT
<213> ORGANISM: Homo sapiens

<400> SEQUENCE: 4

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 5
<211> LENGTH: 40
<212> TYPE: PRT
<213> ORGANISM: Homo sapiens

<400> SEQUENCE: 5

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 6
<211> LENGTH: 41
<212> TYPE: PRT
<213> ORGANISM: Homo sapiens

<400> SEQUENCE: 6

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 7
<211> LENGTH: 41
<212> TYPE: PRT
<213> ORGANISM: Cyprinus carpio

<400> SEQUENCE: 7

Asn Asp Asp Pro Pro Ile Ser Ile Asp Leu Thr Phe His Leu Leu Arg
1               5                   10                  15

Asn Met Ile Glu Met Ala Arg Asn Glu Asn Gln Arg Glu Gln Ala Gly
            20                  25                  30

Leu Asn Arg Lys Tyr Leu Asp Glu Val
        35                  40
```

```
<210> SEQ ID NO 8
<211> LENGTH: 40
<212> TYPE: PRT
<213> ORGANISM: Frog Sauvagine

<400> SEQUENCE: 8

Glu Gly Pro Pro Ile Ser Ile Asp Leu Ser Leu Glu Leu Leu Arg Lys
 1               5                  10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 9
<211> LENGTH: 41
<212> TYPE: PRT
<213> ORGANISM: Dogfish Corticotropin Releasing Factor/Urotensin

<400> SEQUENCE: 9

Pro Ala Glu Thr Pro Asn Ser Leu Asp Leu Thr Phe His Leu Leu Arg
 1               5                  10                  15

Glu Met Ile Glu Ile Ala Lys His Glu Asn Gln Gln Met Gln Ala Asp
            20                  25                  30

Ser Asn Arg Arg Ile Met Asp Thr Ile
        35                  40

<210> SEQ ID NO 10
<211> LENGTH: 112
<212> TYPE: PRT
<213> ORGANISM: Mus musculus

<400> SEQUENCE: 10

Met Thr Arg Trp Ala Leu Val Val Phe Val Val Leu Met Leu Asp Arg
 1               5                  10                  15

Ile Leu Phe Val Pro Gly Thr Pro Ile Pro Thr Phe Gln Leu Leu Pro
            20                  25                  30

Gln Asn Ser Leu Glu Thr Thr Pro Ser Ser Val Thr Ser Glu Ser Ser
        35                  40                  45

Ser Gly Thr Thr Thr Gly Pro Ser Ala Ser Trp Ser Asn Ser Lys Ala
    50                  55                  60

Ser Pro Tyr Leu Asp Thr Arg Val Ile Leu Ser Leu Asp Val Pro Ile
65                  70                  75                  80

Gly Leu Leu Arg Ile Leu Leu Glu Gln Ala Arg Tyr Lys Ala Ala Arg
                85                  90                  95

Asn Gln Ala Ala Thr Asn Ala Gln Ile Leu Ala His Val Gly Arg Arg
            100                 105                 110

<210> SEQ ID NO 11
<211> LENGTH: 38
<212> TYPE: PRT
<213> ORGANISM: Mus musculus

<400> SEQUENCE: 11

Val Ile Leu Ser Leu Asp Val Pro Ile Gly Leu Leu Arg Ile Leu Leu
 1               5                  10                  15

Glu Gln Ala Arg Tyr Lys Ala Ala Arg Asn Gln Ala Ala Thr Asn Ala
            20                  25                  30

Gln Ile Leu Ala His Val
```

-continued

```
                35

<210> SEQ ID NO 12
<211> LENGTH: 38
<212> TYPE: PRT
<213> ORGANISM: Takifugu rubripes

<400> SEQUENCE: 12

Leu Thr Leu Ser Leu Asp Val Pro Thr Asn Ile Met Asn Val Leu Phe
 1               5                  10                  15

Asp Val Ala Lys Ala Lys Asn Leu Arg Ala Lys Ala Ala Glu Asn Ala
            20                  25                  30

Arg Leu Leu Ala His Ile
        35

<210> SEQ ID NO 13
<211> LENGTH: 40
<212> TYPE: PRT
<213> ORGANISM: Rattus norvegicus

<400> SEQUENCE: 13

Asp Asp Pro Pro Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40
```

UROCORTIN PROTEINS AND USES THEREOF

CROSS-REFERENCE TO RELATED APPLICATIONS

This application is a continuation of U.S. patent application Ser. No. 10/973,092 filed Oct. 25, 2004 and allowed; which application is a divisional of U.S. patent application Ser. No. 09/919,473 filed Jul. 31, 2001 and issued as U.S. Pat. No. 6,838,274; which application claims the benefit of U.S. Application No. 60/223,255 filed Aug. 4, 2000 and U.S. Application No. 60/273,969 filed Mar. 7, 2001; all of which applications are incorporated herein by reference in their entireties.

FEDERAL FUNDING LEGEND

This invention was produced in part using funds from the Federal government under grant no. DK-26741. Accordingly, the Federal government has certain rights in this invention.

BACKGROUND OF THE INVENTION

1. Field of the Invention

The present invention relates generally to the fields of neuroendocrinology and the mechanisms involved in stress. More specifically, the present invention relates to novel corticotropin releasing factor-related peptides, urocortin 11 and human urocortin-related protein, which are involved in the stress response.

2. Description of the Related Art

Corticotropin-releasing factor (CRF) is a 41-amino acid peptide best known for its indispensable role in initiating pituitary-adrenal responses to stress, an effect mediated by type 1 CRF receptors (1). In addition, corticotropin-releasing factor is widely distributed in brain, and has been shown repeatedly to participate in the mobilization of complementary autonomic and behavioral adjustments to a variety of threatening circumstances (2, 3). This has fostered the widely held hypothesis that corticotropin releasing factor and its related family of peptides play important roles in regulation of the hypothalamic-pituitary-adrenal axis (HPA) under basal and stress conditions (4, 5). It is also believed that corticotropin-releasing factor is also involved in other neuroendocrine and paracrine responses in many tissues. Members of the CRF family integrate endocrine, autonomic and behavioral responses to stressors. These peptides may also be implicated in the control of appetite, arousal, and cognitive functions. Severe psychological and physiological consequences can occur as a result of the long term effects of stress, such as anxiety disorders, anorexia nervosa and melancholic depression.

Corticotropin-releasing factor family members mediate their biological actions by specifically binding to CRF receptors with high affinities (6, 7). CRF receptors are G-protein coupled receptors that act through adenylate cyclase and are structurally related to the secretin family. This family also includes GRF, VIP, PTH, and the Calcitonin receptor. The CRF receptor gene has 13 exons and several splice variants of this receptor have been found. The CRF-R1 receptor is distributed throughout the brain and is found in sensory and motor relay sites (8). The CRF-R2α is distributed in lateral septum, ventral medial hypothalamus, nucleus of the solitary tract and the dorsal raphe nucleus, which are areas where CRF-R1 is expressed very little or not at all (9). The CRF-R2β is found mostly in peripheral sites including the heart, blood vessels, gastrointestinal tract, epididymis, lung and skin (7, 10). The pharmacology of the two types of receptors differs in that corticotropin-releasing factor has a low affinity for CRF-R2 (Ki=15-100 nM) but high affinity for CRF-R1 (Ki=1-2 nM). Other related peptides such as carp urotensin, frog sauvagine, and urocortin have a high affinity for CRF-R2. CRF-R2 knockout mice demonstrate an increased anxiety-like behavior caused by hypersensitivity to stressors (11).

A number of the cell groups identified as sites of peptide action in eliciting stress-like autonomic and behavioral responses have been found to be lacking or impoverished in the expression of requisite ligand(s), receptor(s) or both (12, 13). This has kindled the search for additional CRF-related signaling molecules, which currently number two ligands, G protein-coupled receptors derived from two distinct genes (CRF-R1 and CRF-R2), and a binding protein, whose function remains incompletely understood (14, 15).

A second mammalian CRF-related neuropeptide, urocortin (Ucn), was recently discovered (16) and shown to be bound with high affinity by both known CRF receptor types, whereas CRF is bound in a highly preferential manner by CRF-R1. Centrally administered urocortin is more potent than CRF in suppressing appetite but less so in generating acute anxiety-like effects and generalized behavioral activation (17). This has been taken to indicate that urocortin might mediate some stress-related effects attributed initially to CRF, at least in part by serving as an endogenous ligand for CRF-R2. This view has been challenged, however, by such observations as that the principal cellular seats of urocortin expression in brain are not recognized as integral components of central stress-related circuitry, and that most major sites of CRF-R2 expression are poorly innervated by urocortin-containing projections (18). These and other findings support the possible existence of one or more additional CRF receptor ligands in the mammalian brain.

The prior art is deficient in the lack of recognition of additional urocortin genes and proteins. The present invention fulfills this longstanding need and desire in the art.

SUMMARY OF THE INVENTION

The rapid advances in the deposition of sequence data for both the human and mouse genomes provide an opportunity to identify new members of many protein families. A novel peptide sequence, Human urocortin-related peptide (URP) was identified from the public human genome database. The urocortin-related peptide sequence contains homology to human Urocortin (44%), carp Urotensin (39%) and human CRF (36%). The synthesized urocortin-related peptide binds with higher affinity to CRF-R2 (Ki=0.5 nM) than to CRF-R1 (Ki=70 nM). Human urocortin-related peptide stimulates ACTH secretion from rat anterior pituitary cells, although with a significantly lower potency compared to urocortin or CRF. Using sequence homology searching tools, a mouse gene encoding a 38-amino-acid peptide was also identified which represents a new member of the CRF family of neuropeptides. This peptide, termed urocortin II (Ucn II), is distinct from the other known family members in that it binds with high selectivity to CRF-R2. Evidence for Urocortin II in the rat brain is provided by immunohistochemistry and in situ hybridization studies using antibodies highly specific for urocortin II.

In one embodiment of the current invention, a DNA sequence encoding urocortin II is provided. This sequence may be selected from the group consisting of: isolated and purified DNA which encodes an urocortin II; isolated and purified DNA which hybridizes at high stringency conditions to the antisense complement of urocortin II DNA under high stringency conditions (defined as membrane washing at high temperature and low salt concentration functionally equivalent to 0.1×SSC at 65° C.); and, isolated and purified DNA encoding urocortin II but which differs in sequence due to the degeneracy of the genetic code. This DNA preferably encodes a protein precursor having the amino acid sequence shown in SEQ ID NO: 10.

In another embodiment of the current invention, the instant invention is directed to a vector capable of expressing the urocortin II. Such a vector consists of DNA encoding urocortin II and regulatory elements necessary for expression of urocortin II in a cell. In a preferred embodiment, this vector encodes a protein of amino acid sequence SEQ ID NO: 11. The instant invention is also directed to a host cell transfected with and expressing urocortin II from such a vector. The protein may be expressed in a cell type selected from bacterial cells, mammalian cells, plant cells and insect cells. In one preferred embodiment, the protein is expressed in *E. coli*.

In yet another embodiment of the instant invention, an isolated and purified human urocortin II protein is provided encoded from DNA as described above. Preferably, the purified human urocortin-related peptide has an amino acid sequence corresponding to SEQ ID NO: 3.

In another embodiment of the instant invention, an antibody directed against the urocortin II protein is provided. This antibody may be a monoclonal antibody.

In yet another embodiment of the instant invention, a pharmaceutical composition is provided comprising urocortin II protein. Such a pharmaceutical composition may be used to reduce body temperature, suppress appetite, and treat or prevent congestive heart failure and various stress-related disorders.

In a further embodiment of the current invention, a DNA sequence encoding human urocortin-related peptide is provided. This sequence may be selected from the group consisting of: isolated and purified DNA which encodes an human urocortin-related peptide; isolated and purified DNA which hybridizes at high stringency conditions to the antisense complement of the human urocortin-related peptide DNA under high stringency conditions (defined as membrane washing at high temperature and low salt concentration functionally equivalent to 0.11×SSC at 65° C.); and, isolated and purified DNA encoding human urocortin-related peptide but which differs in sequence due to the degeneracy of the genetic code. This DNA preferably has the sequence shown in SEQ ID NO: 1 and encodes a protein precursor having the amino acid sequence shown in SEQ ID NO: 2.

In another embodiment of the current invention, the instant invention is directed to a vector capable of expressing the human urocortin-related peptide. Such a vector consists of DNA encoding human urocortin-related peptide and regulatory elements necessary for expression of human urocortin-related peptide in a cell. In a preferred embodiment, this vector encodes a protein of amino acid sequence SEQ ID NO: 3. The instant invention is also directed to a host cell transfected with and expressing an human urocortin-related peptide from such a vector. The protein may be expressed in a cell type selected from bacterial cells, mammalian cells, plant cells and insect cells. In one preferred embodiment, the protein is expressed in *E. coli*.

In yet another embodiment of the instant invention, an isolated and purified human urocortin-related peptide protein is provided encoded from DNA as described above. Preferably, the purified human urocortin-related peptide has an amino acid sequence corresponding to SEQ ID NO: 3.

In another embodiment of the instant invention, an antibody directed against the human urocortin-related peptide protein is provided. This antibody may be a monoclonal antibody.

In yet another embodiment of the instant invention, a pharmaceutical composition is provided comprising human urocortin-related peptide protein. Such a pharmaceutical composition may be used to reduce body temperature, suppress appetite, and treat or prevent congestive heart failure and various stress-related disorders.

In another embodiment of the instant invention, various modifications to the urocortin II and human urocortin-related peptide proteins are described including modification to the sequence and to individual amino acids of the proteins. Modifications also include conjugation of urocortin II and human urocortin-related peptide to fluorescent labels, complexed radionuclides and toxins.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows that a human genomic DNA sequence predicting the existence of a novel peptide related to urocortin and CRF. Genomic sequences were identified in the public database and used to predict the novel sequence of human urocortin-related peptide. The putative start site is at position 1 and the mature peptide sequence is shown in bold text. The predicted signal peptide cleavage sites are indicated with arrows.

FIG. 2 shows a putative Human urocortin-related peptide precursor. The underlined region represents a partial cDNA sequence that was isolated by PCR from a human pancreatic islet cDNA library.

FIG. 3 shows a comparison of human urocortin-related peptide (URP) with human Ucn, urotensin I, CRF, frog sauvagine and dogfish CRF/Uro. Areas of highest homology are inside the white boxes. The number of conserved amino acids is indicated.

FIG. 4A shows the predicted amino acid sequence of Ucn II. The start methionine, marked in bold, is located upstream of the peptide coding region, which is boxed. The complete nucleotide sequence has been deposited in Genbank (accession no. AF331517).

FIG. 4B shows the alignment of mouse Ucn II with homologous human and fish peptides (URPs) and with rat Ucn and rat/human CRF. Residues identical to the mouse Ucn II sequence are boxed. A ■ indicates an amidation site.

FIG. 6B), facial motor nucleus (VII, FIG. 6C) and meninges (men) at the ventral surface of the brain. Other abbreviations: CBL, cerebellum; v3, third ventricle; v4, fourth ventricle. Magnifications: FIGS. 6A and 6B, X75; FIG. 6C, X50.

FIGS. 8A-8C and 8E: Brightfield photomicrographs of immunoperoxidase preparations showing induced Fos expression in rats sacrificed 2 hr after icv injection of 1 µg synthetic mouse urocortin II. Darkfield photomicrographs showing hybridization histochemical localization of CRF-R2 mRNA in regions corresponding to those illustrated in FIGS. 8C and 8E are provided in FIGS. 8D and 8F, respectively. Central urocortin II injection provoked Fos induction primarily in a set of interconnected structures involved in central autonomic and neuroendocrine control, including the parvocellular division of the paraventricular nucleus (FIG. 8A), the central nucleus of the amygdala, (FIG. 8B), and the nucleus of the solitary tract (NTS, FIG. 8C). Among these, only the NTS is a site of CRF-R2 expression (FIG. 8D). Other principal sites of CRF-R2 expression, including the ventromedial nucleus of the hypothalamus (FIG. 8F), failed to show urocortin II-induced Fos expression over the range of peptide doses examined (1-10 µg). All photomicrographs are of 75× magnification.

FIG. 10A shows the mean (±SEM; n=3-6 per group) cumulative nighttime food intake (g) following icv administration of 1 µg CRF, urocortin or urocortin II. Both CRF and urocortin significantly reduced food intake compared to saline-injected controls, beginning at 4 hr post-injection, while the effect of urocortin II was not manifest until 6 hr after treatment. *p<0.002 (CRF and Ucn vs. saline), **p<0.002 (CRF, urocortin, and urocortin II vs. saline). FIG. 10B shows telemetric measures of gross motor activity which were significantly elevated in animals that received icv injections of CRF; neither urocortin nor urocortin II significantly affected motor activity. *p<0.001 (CRF vs. saline).

FIG. 15A shows the total amount of food consumed over the course of experiments. FIG. 15B summarizes the amount of food consumed during each time period of the experiment.

DETAILED DESCRIPTION OF THE INVENTION

Figure 5A:
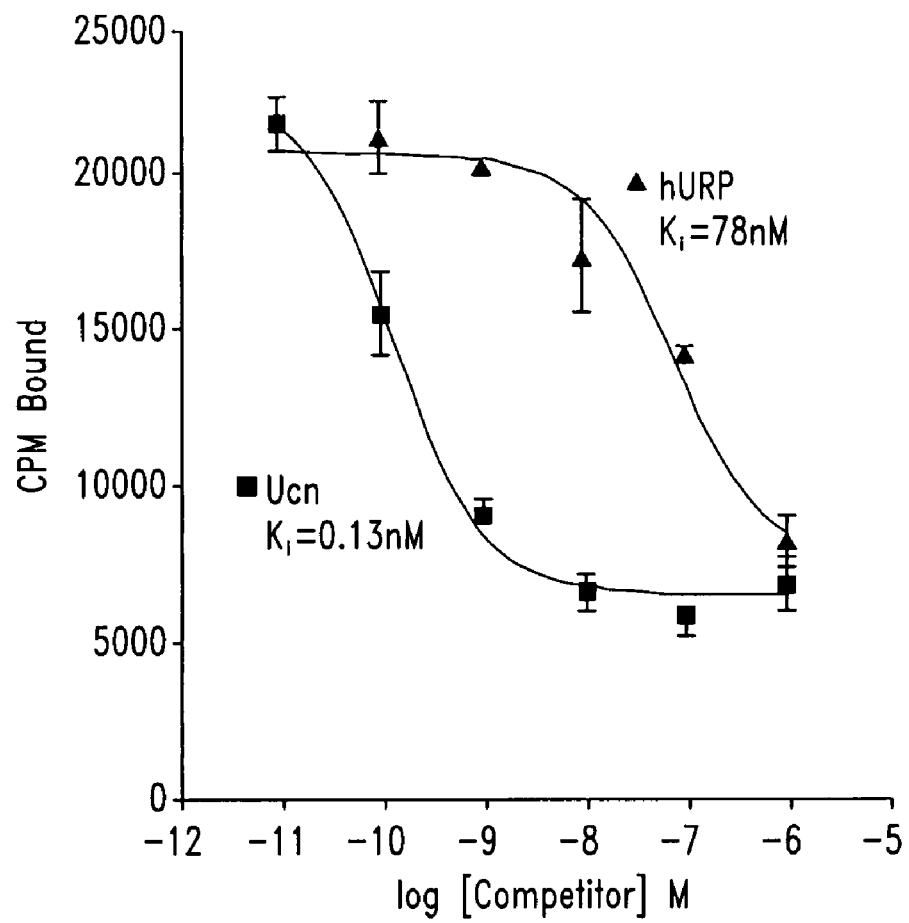
FIGS. 5A and 5B show the human urocortin-related peptide mediated displacement of $^{125}$I-Sauvagine binding to CRFR1 and CRFR2β, respectively. The affinities of Ucn and URP peptides for CRFR1 and CRFR2β_stably expressed in CHO cells were determined by the competitive displacement of the $^{125}$I-Sauvagine. The data is representative of 3 experiments and inhibitory dissociation constant ($K_i$) values (95% confidence limits) were calculated using the Prism program.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins Eds. (1985)]; "Transcription and Translation" [B. D. Hames & S. J. Higgins Eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

All amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

The amino acids described herein are preferred to be in the "L" isomeric form. However, residues in the "D" isomeric form can be substituted for any L-amino acid residue, as long as the desired functional property of immunoglobulin binding is retained by the polypeptide. $NH_2$ refers to the free amino group present at the amino terminus of a polypeptide. COOH refers to the free carboxy group present at the carboxy terminus of a polypeptide.

Nonstandard amino acids may be incorporated into proteins by chemical modification of existing amino acids or by artificial synthesis of a protein. A Nonstandard amino acid refers to an amino acid that differs in chemical structure from the twenty standard amino acids encoded by the genetic code. Post-translational modification in vivo can also lead to the presence of a nonstandard or amino acid derivative in a protein. The N-terminal $NH_2$ and C-terminal COOH groups of a protein can also be modified by natural or artificial post-translational modification of a protein.

Proteins may be modified by amino acids substitutions. Often, some changes result in significant changes in the activity of proteins while other have little or no effect. Conservative substitutions are least likely to drastically alter the activity of a protein. A "conservative amino acid substitution" refers to replacement of amino acid with a chemically similar amino acid, i.e. replacing nonpolar amino acids with other nonpolar amino acids; substitution of polar amino acids with other polar amino acids, acidic residues with other acidic amino acids, etc., Examples of preferred conservative substitutions are set forth in Table 1:

TABLE 1

| Original Residue | Preferred Conservative Substitutions | Most Preferred Conservative Substitution |
|---|---|---|
| Ala (A) | Val; Leu; Ile | Val |
| Arg (R) | Lys; Gly; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn; Gln; Lys; Arg | Arg |
| Ile (I) | Leu; Val; Met; Ala; Phe; Nle | Leu |
| Leu (L) | Ile; Val; Met; Ala; Phe; Nle | Ile |
| Lys (K) | Arg; Gln; Asn | Arg |
| Met (M) | Leu; Phe; Ile | Leu |
| Phe (F) | Leu; Val; Ile; Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp; Phe; Thr; Ser | Phe |
| Val (V) | Ile; Leu; Met; Phe; Ala; Nle | Leu |

"Chemical derivative" refers to a subject polypeptide having one or more residues chemically derivatized by reaction of a functional side group. Such derivatized polypeptides include, for example, those in which free amino groups have been derivatized to form amine hydrochlorides, p-toluene sulfonyl groups, carbobenzoxy groups, t-butylocycarbonyl groups, chloroacetyl groups, or formyl groups. Free carboxyl groups may be derivatized to form salts, methyl and ethyl esters or other types of esters or hydrazides. Chemical derivatives may include those peptides which contain one or more naturally occurring amino acids derivatives of the twenty standard amino acids. For example, 4-hydroxyproline may be substituted for serine; and ornithine may be substituted for lysine. Peptides embraced by the present invention also include peptides having one or more residue additions and/or deletions relative to the specific peptide whose sequence is shown herein, so long as the modified peptide maintains the requisite biological activity.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single-stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence, which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited, to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerise in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA"

boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, which communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns or synthetic sequences having codons different than the native gene). Allelic variations or naturally occurring mutational events do not give rise to a heterologous region of DNA as defined herein.

The labels most commonly employed for these studies are radioactive elements, enzymes, chemicals that fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

As used herein, the term "host" is meant to include not only prokaryotes but also eukaryotes such as yeast, plant and animal cells. A recombinant DNA molecule or gene that encodes a protein of the present invention can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

In general, expression vectors containing promoter sequences that facilitate the efficient transcription of the inserted DNA fragment are used in connection with the host. The expression vector typically contains an origin of replication, promoter(s), terminator(s), as well as specific genes that are capable of providing phenotypic selection in transformed cells. The transformed hosts can be fermented and cultured according to means known in the art to achieve optimal cell growth.

Methods well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

The current invention is directed to a DNA sequence encoding urocortin II. This sequence may be an isolated and purified DNA that encodes an urocortin II. Alternatively, it may be an isolated and purified DNA which hybridizes at high stringency conditions to the antisense complement of the urocortin II DNA under high stringency conditions (defined as membrane washing at high temperature and low salt concentration functionally equivalent to 0.1×SSC at 65° C.). Finally, the DNA may be an isolated and purified DNA encoding urocortin II but which differs in sequence due to the degeneracy of the genetic code: This DNA will preferably encode a protein of amino acid sequence SEQ ID NO: 10 or amino acid SEQ ID NO: 11.

The instant invention is also directed to a vector capable of expressing the urocortin II. Such a vector consists of DNA encoding urocortin II and regulatory elements necessary for expression of urocortin II in a cell. In a preferred embodiment, this vector encodes a protein of amino acid sequence SEQ ID NO: 10 or amino acid SEQ ID NO: 11. The instant invention is also directed to a host cell transfected with and expressing an urocortin II from such a vector. The protein may be expressed in a cell type selected from bacterial cells, mammalian cells, plant cells and insect cells. In a preferred embodiment, the protein is expressed in *E. coli*.

The instant invention is also directed to an isolated and purified urocortin II protein encoded from DNA as described above. Preferably, the purified urocortin II has an amino acid sequence corresponding to SEQ ID NO: 10 or SEQ ID NO: 11.

The instant invention is also directed to an antibody directed against the urocortin II protein. This antibody is preferably a monoclonal antibody.

Furthermore, the instant invention is directed to a pharmaceutical composition comprising the urocortin II protein and a pharmaceutically acceptable carrier. Such a pharmaceutical composition may be used to reduce body temperature, suppress appetite, treat or prevent congestive heart failure, treat stress and anxiety, and alter undesirably low levels of ACTH secretion.

The current invention is also directed to a DNA sequence encoding human urocortin-related peptide. This sequence may be an isolated and purified DNA that encodes human urocortin-related peptide. Alternatively, it may be an isolated and purified DNA which hybridizes at high stringency conditions to the antisense complement of the human urocortin-related peptide DNA under high stringency conditions (defined as membrane washing at high temperature and low salt concentration functionally equivalent to 0.1×SSC at 65° C.). Finally, the DNA may be an isolated and purified DNA encoding human urocortin-related peptide but which differs in sequence due to the degeneracy of the genetic code. This DNA will preferably have the sequence shown in SEQ ID NO: 1 and will preferably encode a precursor protein of amino acid sequence SEQ ID NO: 2 which is proteolytically processed to a protein of amino acid sequence SEQ ID NO: 3.

The instant invention is also directed to a vector capable of expressing the human urocortin-related peptide. Such a vector consists of DNA encoding human urocortin-related peptide and regulatory elements necessary for expression of human urocortin-related peptide in a cell. In a preferred embodiment, this vector encodes a protein of amino acid sequence SEQ ID NO: 3. The instant invention is also directed to a host cell transfected with and expressing human urocortin-related peptide from such a vector. The protein may be expressed in a cell type selected from bacterial cells, mammalian cells, plant cells and insect cells. In a preferred embodiment, the protein is expressed in *E. coli*.

The instant invention is also directed to an isolated and purified human urocortin-related peptide protein is provided encoded from DNA as described above. Preferably, the purified human urocortin-related peptide has an amino acid sequence corresponding to SEQ ID NO: 3.

The instant invention is also directed to an antibody directed against the human urocortin-related peptide protein is provided. This antibody is preferably a monoclonal antibody.

Furthermore, the instant invention is directed to a pharmaceutical composition comprising the human urocortin-related peptide protein and a pharmaceutically acceptable carrier. Such a pharmaceutical composition may be used to reduce body temperature, suppress appetite, treat or prevent congestive heart failure, treat stress and anxiety, and alter undesirably low levels of ACTH secretion.

The instant invention is also directed to urocortin II or human urocortin-related peptide mutated to contain a tyrosine residue, which for radioiodination of the protein. One particular modification is the addition of a sequence consisting of Tyr-Gly to the N-terminal end of urocortin II or human urocortin-related peptide.

The instant invention is also directed to deletion mutants of urocortin II or human urocortin-related peptide. A particularly useful deletion is a deletion of one to five amino acids from the N-terminal end of the protein.

The instant invention is also directed to urocortin II or human urocortin-related peptide protein in which the standard "L-form" isomeric amino acids are replaced with "D-form" isomeric amino acids. In human urocortin-related protein, substitution of the isoleucine residue corresponding to position 9 of SEQ ID NO: 3 with D-isoleucine, D-phenylalanine, and D-Leucine or other D-form amino acids is particularly useful. Another useful substitution is the replacement of the glutamic acid residue at position 17 of SEQ ID NO: 3 or SEQ ID NO: 11 with D-glutamic acid.

The instant invention is also directed to urocortin II or human urocortin-related peptide in which various amino acids have been replaced with nonstandard amino acids $C_\alpha$-methylated leucine, $C_{60}$-methylated alanine, N-im-benzyl-histidine, 4-hydroxyproline, 5-hydroxylysine, 3-methylhistidine, homoserine, and ornithine are examples of such nonstandard amino acids.

The instant invention is also directed to urocortin II or human urocortin-related peptide protein having an acylated N-terminus. This protein acylation may be used to link a molecule such as fatty acid at the N-terminus of the protein to protect Ucn II or URP from enzymatic degradation or to change various properties of the protein such as its hydrophilicity/hydrophobicity. These modification may be used alter the duration or bioavailability of the protein in vivo.

The instant invention is also directed to urocortin II or human urocortin-related peptide protein that has been modified to contain a fluorescent label for use in imaging or biological assays.

The instant invention is also directed to a urocortin II or human urocortin-related peptide protein conjugated with a complexing agent for radionuclides. Ucn II complexed to a radionuclide may be useful for scintigraphy or in various assays.

The instant invention is also directed to urocortin II or human urocortin-related peptide conjugated to a toxin. The resulting toxic conjugate can be used for the targeted destruction of CRF receptor-bearing cells.

The following examples are given for the purpose of illustrating various embodiments of the invention and are not meant to limit the present invention in any fashion.

EXAMPLE 1

Identification of Human Urocortin-Related Protein

In an effort to identify novel CRF-R ligands, a hidden Markov model (HMM) was constructed from a clustal W alignment of known CRF family proteins, including rat/human CRF, rat Ucn, human Ucn, frog sauvagine, and whitesuckerfish urotensin I, using the HMMER software package. (Sean Eddy, Department of Genetics, Washington University, St. Louis, Mo.; see ref. 19). This HMM was used to search the public human genome database and a BAC (Genbank accession no. AC005903) derived from chromosome 3p21.3-4 was identified that contained a 109 bp region exhibiting significant sequence homology but which was not a part of a previously identified gene. This region was extended to 621 bp with the identification of a human EST clone that overlapped with this sequence (Genbank accession No. BE622276). The human sequence, however, lacks a consensus proteolytic cleavage site that would allow for C-terminal processing of the peptide. Therefore, the protein was designated as a human urocortin-related peptide (hURP) sequence. FIG. 1 shows the nucleotide (SEQ ID NO: 1) sequence of the predicted open reading frame of the human URP protein. This gene encodes a peptide of amino acid sequence SEQ ID NO: 2.

To confirm the existence and sequence of the human urocortin-related peptide gene, oligonucleotide primers similar to those used to amplify the human urocortin-related peptide sequence from the genomic clone were used to isolate a partial cDNA fragment by PCR from a human pancreatic islet cDNA library. This fragment was also subcloned into pGEM vector and sequenced. The sequence of the cDNA corresponded to a portion of the genomic sequence. The partial cDNA sequence corresponds to the underlined sequence in FIG. 2. The sequences shown in FIGS. 1 and 2 encode a polypeptide precursor of the human urocortin-related peptide. The first 19 nucleotides of human urocortin-related peptide encode a signal peptide that is cleaved during the post-translational modification of the protein to yield mature human urocortin-related peptide of amino acid sequence:

(SEQ ID NO: 3)
I V L S L D V P I G L L Q I L L E Q A R A R A A R
E Q A T T N A R I L A R V G H C-NH$_2$

FIG. 3 shows the results of a homology comparison between amino acids 72-109 of human urocortin-related peptide and equivalent segments of human urocortin, human urotensin I, human corticotrophin releasing factor (CRF), frog sauvagine, and dogfish CRF/Uro. The homology in this region ranges from 26% to 42%.

EXAMPLE 2

Identification of Mouse Urocortin II

Fragmentary CDNA probes based on the human gene sequence specifically cross-hybridized with rat tissue (brain), suggesting that a reasonable degree of homology existed between the two species. Based on this human sequence, primers were designed to identify the homologous mouse gene by the Rapid Amplification of cDNA Ends (RACE) method. RACE ready cDNA was prepared from mouse whole-brain poly(A+) RNA using the SMART RACE cDNA amplification kit (Clontech). PCR reactions were run under low stringency (low $T_m$) conditions in an effort to allow for the maximal heterologous priming. First round amplification was carried out using a touchdown protocol (94°, 30 sec; increment from 70° to 55°, 30 sec; 72°, 3 min) followed by a second round of amplification with multiple sets of nested primers (94°, 20 sec; 55°, 20 sec; 72°, 3 min). Candidate PCR products were cloned into pCRII-TOPO (Invitrogen) for sequencing of both strands. Candidate 5' and 3' reaction products were identified based on their predicted size (deduced from the human sequence), cloned and sequenced.

The predicted amino acid sequence for the mouse Ucn II is listed in FIG. 4A. The gene encodes a 112 amino acid precursor, and the C-terminus includes the coding region for the putative 38 amino acid mature peptide, indicated in the boxed region (FIG. 4A). The C-terminal portion of the coding sequence is followed by a glycine and paired basic residues (R-R), presumed to be involved in amidation and cleavage from the precursor, respectively.

Two other putative or known urocortin-related peptides exist: the human one, whose peptide sequence was deduced from the published human EST, as well as a recently cloned (20) pufferfish URP (from Takifugu rubripes). Alignment with the human and fish urocortin-related peptides, rat Ucn, and rat/human CRF is shown in FIG. 4B. At the amino acid level, the coding region of mouse Ucn II displays 77% and 45% homology with the human and fish urocortin-related peptides, respectively. Mouse Ucn II is comparably related to known members of this peptide family, sharing 36% and 44% amino acid identity with rat CRF and rat UCN, respectively. Allowing for conservative substitutions, relatedness increases to 62% (with CRF) and 59% (Ucn).

EXAMPLE 3

Peptide Synthesis

Murine Ucn II and human Ucn-related peptide were synthesized manually using the solid phase approach, a methylbenzhydryl amine resin and the Boc-strategy (21). Trifluoroacetic acid, 60% in dichloromethane, was used to remove the Boc group. Main chain assembly was mediated by diisopropylcarbodiimide. The peptides were cleaved and deprotected in hydrofluoric acid and purified using RP-HPLC and three solvent systems (triethylammonium phosphate at pH 2.25 and 6.5 and/or 0.1% TFA) (22). Peptides were greater than 95% pure using independent HPLC and CZE criteria. Mass spectra was used to confirm the composition of the preparations.

EXAMPLE 4

Receptor Activation by Ucn II

The affinity of Ucn II to the CRF-R1 and CRF-R2 receptors was evaluated using a radioreceptor assay. Crude membrane fractions were prepared from CHO cells stably expressing either cloned CRF-R1 or CRF-R2β. Test peptides and the radioligand, $^{125}$I-[Tyr$^0$, Glu$^1$, Nle$^{17}$]-sauvagine, were diluted in assay buffer (20 mM HEPES, 2 mM EGTA, 0.1% BSA, 10% sucrose, pH 7.6) and combined with the receptor membrane preparations in MAGV microtiter plates (Millipore) pre-coated with 0.1% polyethylene imine. The reaction mixture was incubated for 90 min at room temperature followed by rapid washing twice with assay buffer and filtration. The radioligand complex was quantified by gamma radiation counting. Inhibitory binding constants were determined using Prism software. The results are summarized in Table 2.

TABLE 2

Binding properties and functional activities of select CRF receptor ligands.

| | CRF-R1 | | CRF-R2 | |
|---|---|---|---|---|
| Peptide | Avg. $K_i$ (nM) (Binding) | Avg EC$_{50}$ (nM) (cAMP) | Avg. $K_i$ (nM) (Binding) | Avg EC$_{50}$ (nM) (cAMP) |
| Urocortin II (mouse) | >100 | >100 | 0.66 (0.13-3.3) | 0.14 (0.03-0.52) |
| URP (human) | >100 | >100 | 0.50 (0.2-1.16) | 0.42 (0.16-1.1) |
| Urocortin (rat) | 0.32 (0.14-0.77) | 0.29 (0.12-0.70) | 0.62 (0.14-2.8) | 0.17 (0.043-0.68) |
| Sauvagine (frog) | 0.94 (0.49-1.8) | N/A | 1.7 (0.77-3.9) | N/A |

The values were determined from 3-6 independent experiments using stably transfected CHO cells or their membranes for each test peptide. EC$_{50}$ and $K_i$ values were determined using Prism software. Their log$_{10}$ values were averaged (γ). The average EC$_{50}$ or $K_i$ was taken to be $10^\gamma$. The standard deviation of the log$_{10}$ values was calculated (σ). The ranges given were taken to be: [$(10^\gamma)10^\sigma$ or $10^\gamma/10^\sigma$].

Compared to urocortin, Ucn II was at least 1000-fold less effective at competing for binding of labeled sauvagine to the CRF-R1 whereas it was nearly equipotent to Ucn in competing for binding to CRF-R2. This significant selectivity for the type 2 receptor was seen also in receptor activation as measured by accumulation of intracellular cAMP. Stably transfected CHO cells (cultured in DMEM/10% FBS) were plated into 48-well tissue culture dishes (Costar) and allowed to recover for 24 hours. The medium was changed to DMEM/0.1% FBS at least two hours before treatment. The cells were preincubated for 30 min with 0.1 mM 3-isobutyl-1-methylxanthine and then exposed to peptides for 20 min at 37° C. Intracellular cAMP was extracted and measured in duplicate from triplicate wells using a RIA kit (Biomedical Technologies). In the cAMP assay, Ucn II displayed a comparable efficacy for CRF-R2 as did Ucn (Table 2). The extremely low affinity of Ucn II for CRF-R1 precluded a determination of its efficacy on this receptor.

EXAMPLE 5

Receptor Binding Experiments with Human URP

Membranes were prepared as described above (29). Binding was performed in 96-well 0.2 μm Durapore plates using the vacuum filtration multiscreen assay system (Millipore). Each well contained a total volume of 200 μl consisting of 50 μl of binding buffer (10% Sucrose, 0.1% BSA, 2 mM EGTA, 20 mM HEPES buffer, pH 7.5); 50 μl of unlabeled competitor (urocortin or human urocortin-related peptide) at various dilutions in binding buffer; 50 μl $^{125}$I-Sauvagine at a concentration of 150,000 cpm/well; and, 50 μl of cell membranes. Plates were incubated for 1 hour at room temperature, vacuum-filtered, washed twice with binding buffer, and allowed to dry. Individual filters were punched out and counted using a gamma counter.

Figure 5B:
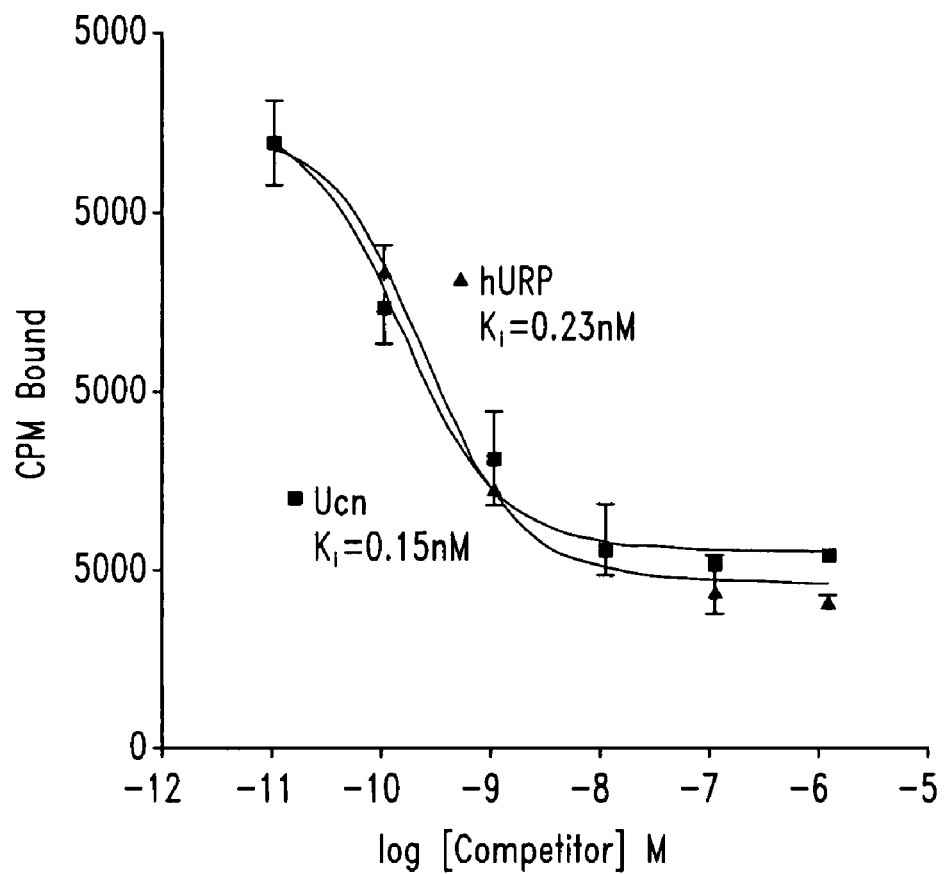

Human urocortin-related peptide mediated displacement of $^{125}$I-Sauvagine binding to CRFR1 and CRFR2β stably expressed in CHO cells is shown in FIG. 5. From this data, human urocortin-related peptide was found to have a disassociation constant ($K_i$) of 78 nM for CRF-R1 and 0.23 nM for CRF-R2β. Ucn, on the other hand, had a disassociation constant of 0.13 nm for CRF-R1 and 0.15 nM for CRF-R2β. Therefore, human urocortin-related peptide is much more specific for the corticotropin releasing factor type II receptor than urocortin.

EXAMPLE 6

Ucn II mRNA Expression

Hybridization histochemistry was carried out to analyze the pattern of Ucn II mRNA expression in mouse and rat brain. Animals were deeply anesthetized with chloral hydrate (350 mg/kg, ip) and perfused via the ascending aorta with saline followed by ice-cold 4% paraformaldehyde in 0.1% borate buffer pH 9.5. Brains were postfixed for 16 hr and cryoprotected overnight in 10% sucrose in 0.1M phosphate buffer. Four (mice) or six (rats) series of 30 μm-thick frozen sections were cut using a sliding microtome, collected in cold ethylene glycol-based cryoprotectant and stored at −20° C. until histochemical processing.

In situ hybridization was performed using $^{35}$S-labeled antisense and sense (control) cRNA probes (23), constructed by first linearizing the TOPO-II plasmid containing the mouse cDNA. Probes were labeled to specific activities of 1-3×10$^9$ dpm/μg, applied to slides at concentrations of about 10$^7$ cpm/ml and hybridized overnight at 56° C. under high stringency (50% formamide). Final washes were carried out in 15 mM NaCl/1.5 mM sodium citrate at 65-68° C. Slides were then dehydrated and exposed to x-ray film (β-Max; Kodak) for 16 hr and then coated with Kodak NTB-2 liquid emulsion and exposed at 4° C. for 21-28 days.

Figure 6A:
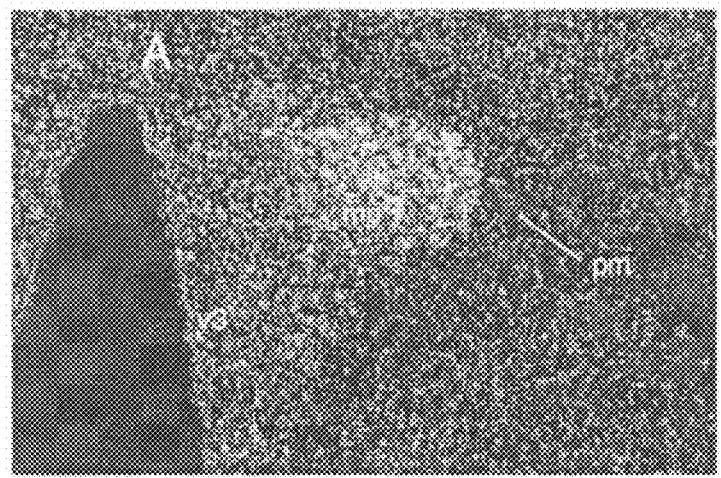
FIGS. 6A-6C show urocortin II mRNA expression in the rat brain. Darkfield photomicrographs showing labeling (white grains) observed over select regions using an isotopically labeled antisense cRNA probe generated from a mouse urocortin II cDNA. Positive hybridization signals are seen over the paraventricular nucleus of the hypothalamus (FIG. 6A), principally over its magnocellular division (pm), with more diffuse signal seen over the parvocellular aspect (mp), and broadly over the locus coeruleus (LC.
Figure 6B:
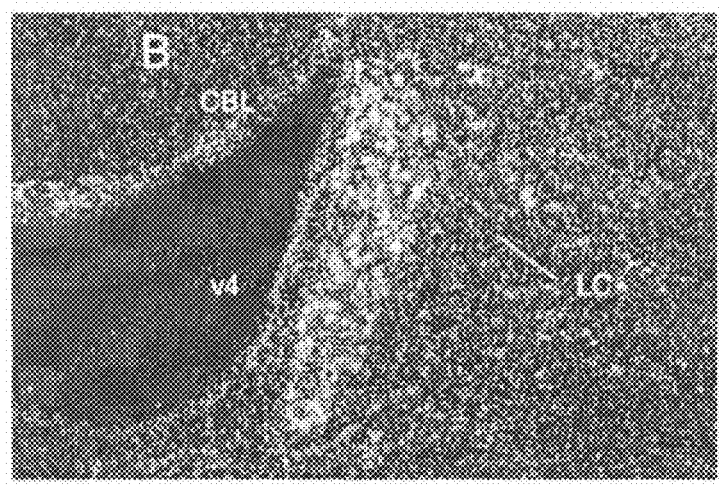
Figure 6C:
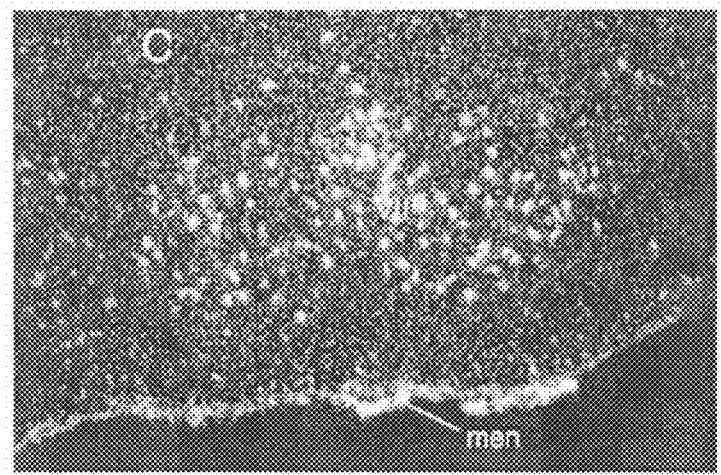

Hybridization histochemistry revealed a consistent and restricted pattern of Ucn II mRNA expression in mouse and rat brain. Sense-strand runoffs labeled to similar specific activities as antisense probes failed to yield above-background hybridization signals. The observed distribution of Ucn II mRNA was seen to be predominantly subcortical, with major sites of expression including stress-related cell groups such as the paraventricular, supraoptic and arcuate nuclei of the hypothalamus, and the locus coeruleus of the rostral pons (FIG. 6). Motor nuclei of the brainstem (trigeminal, facial, hypoglossal), as well of the spinal ventral horn, were also identified as sites of Ucn II mRNA expression. Among non-neuronal elements, positive hybridization signals were observed consistently over the meninges, but not the choroid plexus or ependyma. No clear suggestion of Ucn II mRNA expression by glial elements was evident.

EXAMPLE 7

Urocortin-Related Peptide Expression in the Primate Brain

Figure 7:
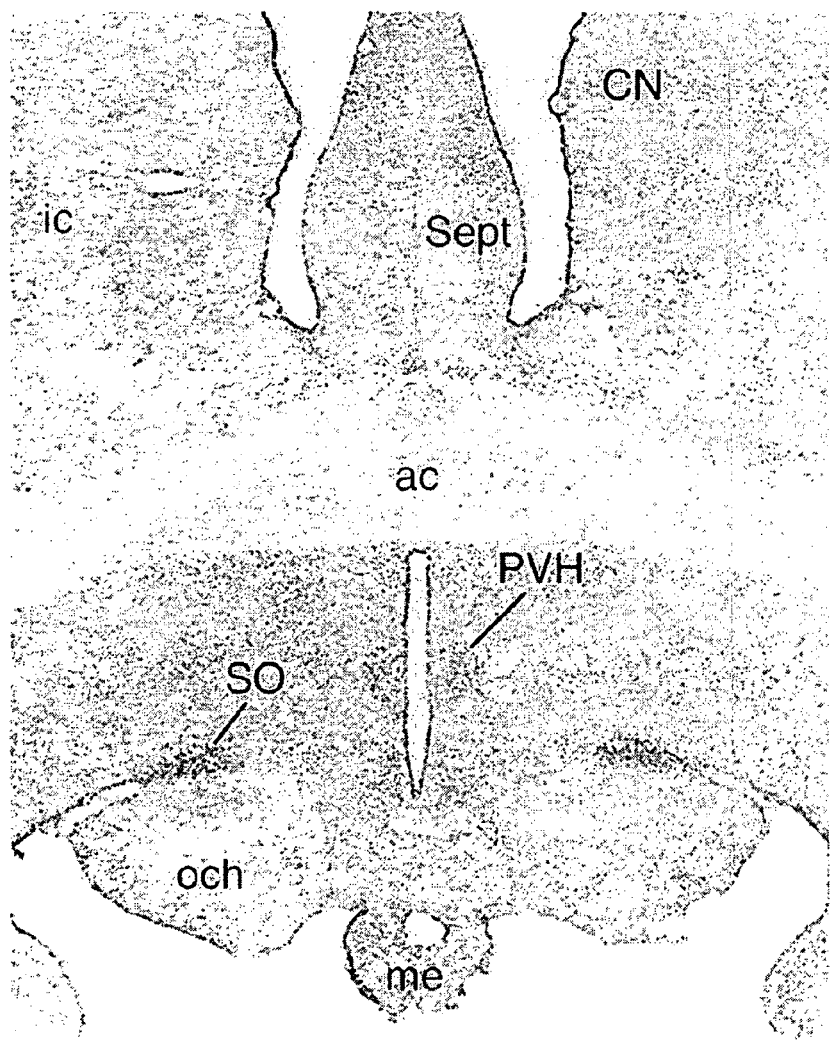
FIG. 7 shows an autoradiogram of human urocortin-related peptide expression in the primate hypothalamus. PVH, paraventricular nuclei; SO, supraoptic nuclei; CN, caudate nucleus; och, optic chiasm; me, median eminence; ac, anterior commissure; ic, internal capsule; Sept, septum.

The expression of human urocortin-related peptide in the primate brain was examined by in situ hybridization. The in situ hybridization was performed on sections of brain tissue from *Macaca fascicularis* using an $^{35}$S-labeled antisense cRNA probe corresponding to about 400 base pairs of human urocortin-related peptide. The probe was applied to the slide at a concentration of $10^7$ cpm/ml and hybridization was allowed to proceed overnight. After hybridization, the slide were treated with 20 μg/ml of ribonuclease A for 30 minutes at 37° C. and washed in 15 nM NaCl/1.5 mM sodium citrate/50% formamide at 70° C. Slides were dehydrated and exposed to X-ray film (BetaMax; Kodak) for 24 hours. A sample autoradiogram is shown in FIG. 7. Positive signal for URP is observed in the paraventricular (PVH) and supraoptic nuclei of the primate hypothalamus.

EXAMPLE 8

Ucn II-Induced Fos Expression

To identify cell groups responsive to central Ucn II administration, and to evaluate the extent to which these may conform to sites of CRF-R2 expression, the induced expression of the immediate-early gene product, Fos, in response; to icv peptide administration was monitored. Adult male Sprague-Dawley rats (250-300 g at start of experiments) and C57 BU6 mice (25-40 g) were housed in a colony room on a 12:12 light:dark cycle, and with free access to food and water prior to experimentation. For intracerebroventricular (icv) injections, rats were anesthetized with ketamine/xylazine/acepromazine and stereotaxically implanted with a 26 ga guide cannula terminating in the lateral ventricle. For intravenous (iv) administration of peptides, animals were fitted with indwelling jugular venous catheters. Rats that received icv injections were also implanted intra-abdominally with a transmitter to remotely monitor gross activity levels and body temperature (Mini-Mitter). After surgery, animals were allowed to recover for 7 days prior to any experimentation, during which time they were handled daily. All procedures were approved by the Institutional Animal Care and Use Committee of the Salk Institute.

To monitor induced patterns of Fos expression, rats were injected at 10 am, either icv or iv with synthetic Ucn II (1, 5 or 10 μg/animal in 2 μl saline for icv injections or 200 μl for iv administration), or vehicle alone, and perfused two hours later. To monitor the effect of peptide administration on food intake, animals were injected icv with synthetic mouse Ucn II, rat Ucn, or rat/human CRF 30 min prior to lights out. Consumption was then measured hourly for 6 hrs and at 12 hrs. Data were analyzed using repeated measures analysis of variance (ANOVA), with the Bonferoni correction for multiple comparisons applied as warranted.

For immunohistochemistry, tissue was pretreated sequentially with 0.3% hydrogen peroxide and 1% sodium borohydride. It was then permeabilized with PBS/0.2% triton X-100, and incubated with primary antiserum for 48 hr in PBS/2% blocking serum. Fos immunoreactivity was localized using a polyclonal antiserum raised in rabbit against an N-terminal synthetic fragment of human Fos protein (Santa Cruz Biotechnology, 1:5 K). Localization was performed using a conventional avidin-biotin immunoperoxidase method with nickel enhancement, as described (24).

Figure 8:
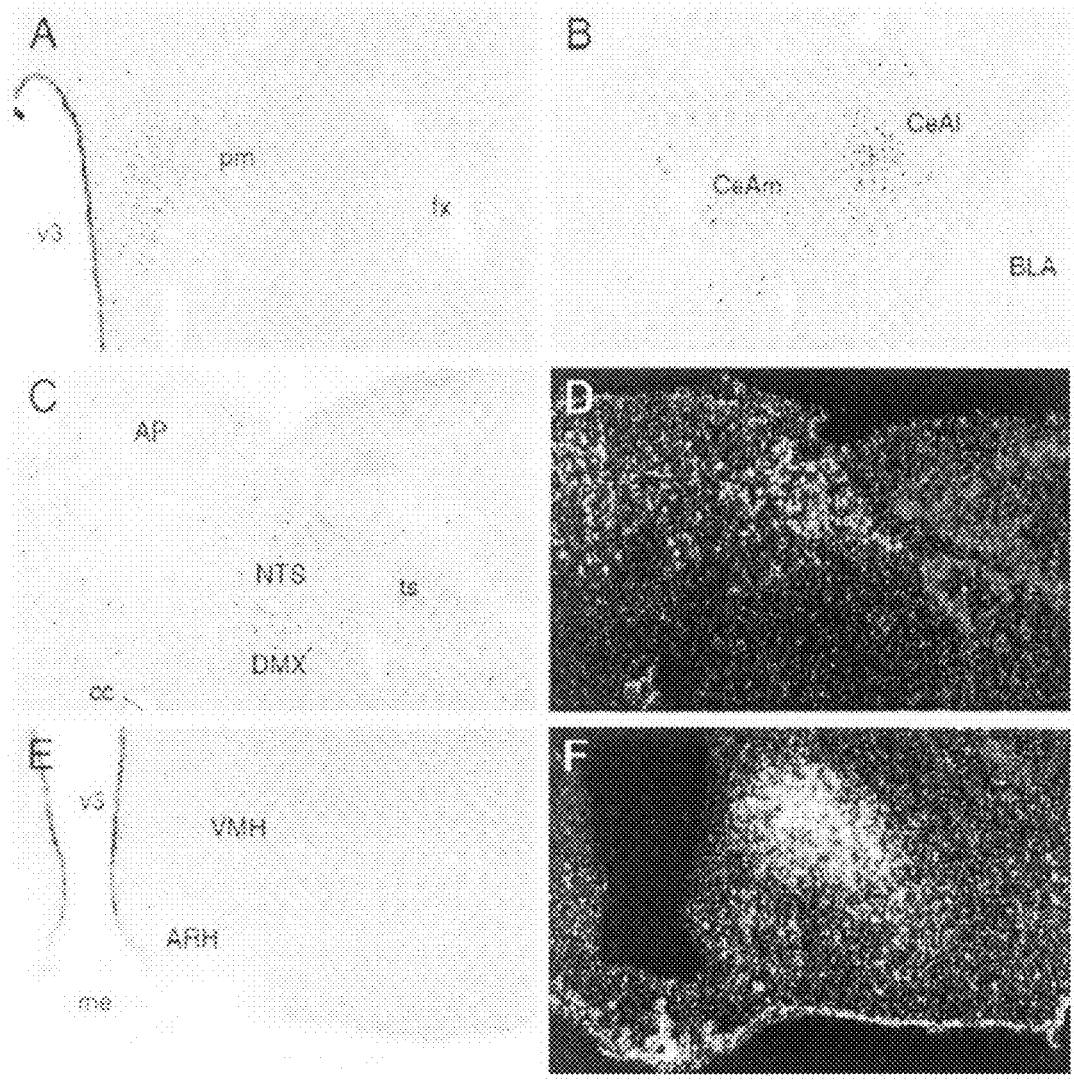
FIGS. 8A-8F show cellular activation patterns in response to central urocortin II microinjection.

Injection of 1 μg synthetic Ucn II gave rise to activational responses that were most salient in a group of interconnected structures involved in central autonomic control (25, 26). These included discrete aspects of the bed nucleus of the stria terminalis, the central nucleus of the amygdala, the paraventricular nucleus of the hypothalamus (PVH), parabrachial nucleus and nucleus of the solitary tract (NTS; FIG. 8). Of these, only the NTS has been described as a locus of CRF-R2 expression (27). Fos induction in other major sites of CRF-R2 expression, including the lateral septum, midbrain raphe nuclei and the ventromedial nucleus of the hypothalamus (27, 28), was not distinguishable from that seen in saline-injected controls. Higher doses of peptide (5 or 10 μg) provoked more robust activational responses of similar distribution.

To control for potential systemic effects of icv injections, a similar range of Ucn II doses was given intravenously to separate groups of rats. Only the highest (10 μg) dose gave rise to Fos induction that was clearly above control levels. Although the pattern was similar to that seen in response to central injections, neither the number of labeled cells nor their staining intensity approached that seen reliably following icv injections of 1 μg Ucn II.

EXAMPLE 9

Urocortin-Related Peptide Stimulated Fos Expression in the Brain

Activation of central stress-related cells groups by human urocortin-related peptide was examined by detection of the Fos gene product in the cells following injection with human urocortin-related peptide. Rats were implanted with guide cannulae in a lateral cerebral ventricle seven days prior to experimentation. On the day of testing, the rats were injected with 5 μg synthetic human urocortin-related peptide in 5 μl of sterile saline. The rats were sacrificed two hours later and slides of various brain sections were prepared. The slides were stained by immunoperoxidase localization of Fos-immunoreactivity using a polyclonal serum raised in rabbit against residues 3-16 of the human Fos protein.

Figure 9:
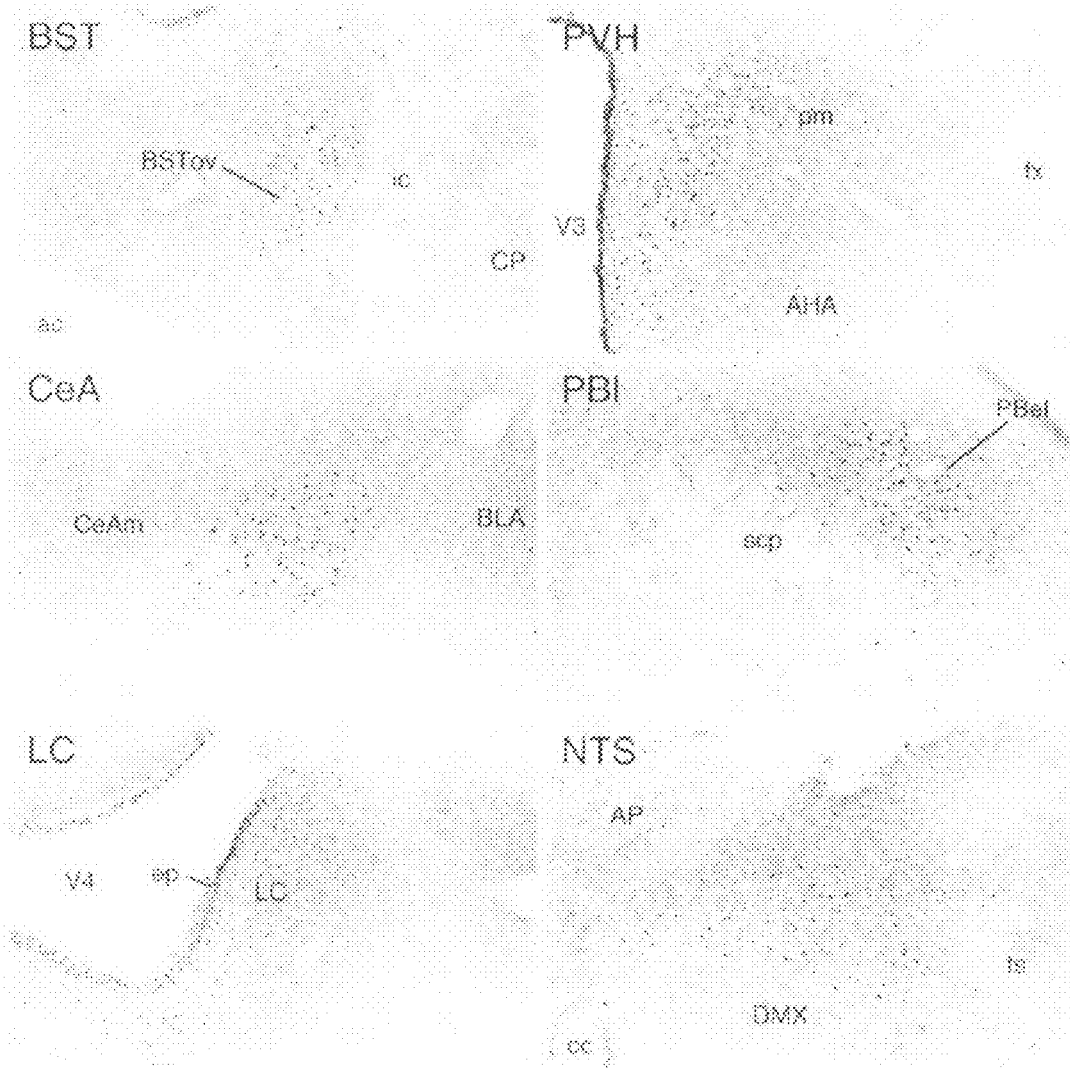
FIG. 9 shows the activation of central stress-related cell groups following central injection of human urocortin-related peptide by examining stimulation of nuclear FOS expression in the stria terminalis (BST), paraventricular nucleus of the hypothalamus (PVH), central nucleus of the amygdala (CeA), the lateral parabrachial nucleus (PBl), the locus coeruleus (LC) and the nucleus of the solitary tract (NTS). BSTov, bed nucleus of the stria terminalis (oval subnucleus); ic, internal capsule; CP, caudoputamen; ac, anterior commissure; V3, third ventricle; AHA, anterior hypothalamic area; pm, posterior magnocellular part (paraventricular nucleus); fx, fornix; CeAm, central nucleus of the amygdala (medial part); BLA, basolateral nucleus of the amygdala; scp, superior cerebellar peduncle; PBel, parabrachial nucleus (external lateral part); V4, fourth ventricle; ep, ependyma; AP, area postrema; DMX, dorsal motor nucleus of the vagus; ts, solitary tract; and, cc, central canal.

As shown in FIG. 9, Fos-immunoreactivity was detected in the bed nuclease of the stria terminalis (BST), the paraventricular nucleus of the hypothalamus (PVH), the central nucleus of the amygdala (CeA), the lateral parabrachial nucleus (PBT), the locus coeruleus (LC), and nucleus of the solitary tract (NTS). Each of these sites has been previously implicated as a site of CRF-related peptide activity.

EXAMPLE 10

Behavioral Effects of Ucn II

Figure 10A:
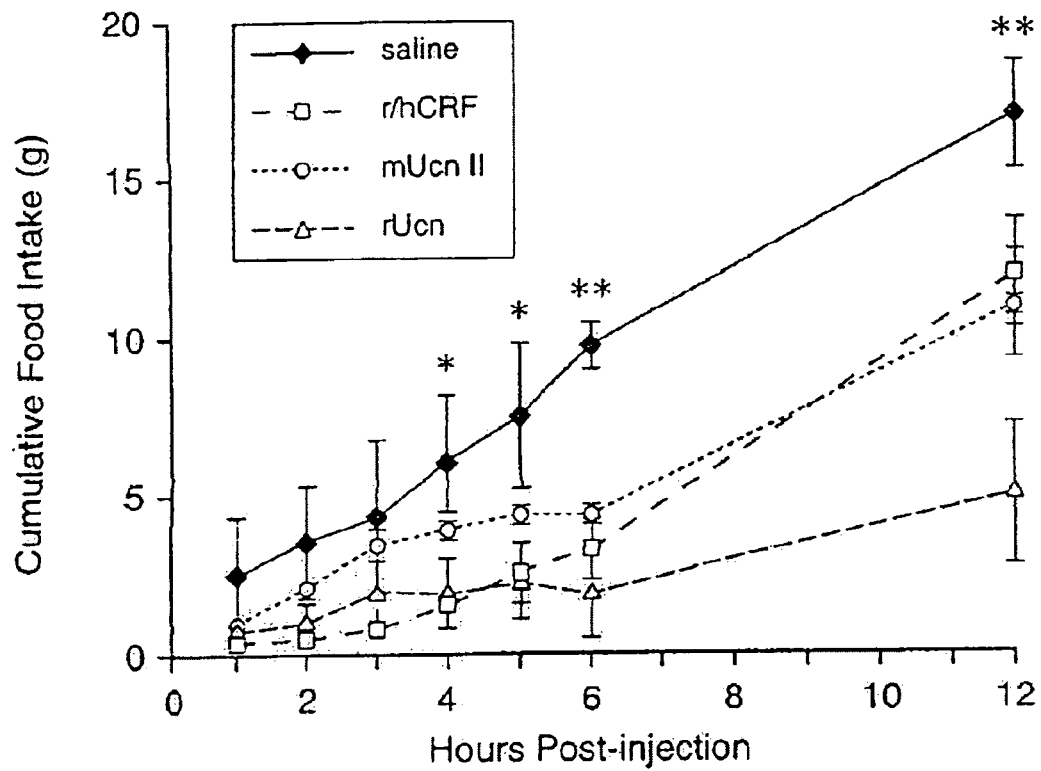
FIGS. 10A and 10B show the effects of central urocortin II on food intake and gross motor activity.

Like CRF and Ucn, Ucn II is also capable of acting centrally to inhibit food intake (FIG. 10A). Measures from separate groups of rats injected with these peptides (1 μg, icv) at the beginning of the nocturnal phase of their day-night cycle manifest a significant interaction between treatment and time point [F (18,95)=4.22, p<0.0001], with both main effects also achieving reliability. All three peptides significantly reduced food intake over the 12 hr interval, with the degree of suppression ranging from 30% (CRF) to 35% (Ucn II) to 70% (Ucn). These effects tended to be distributed differentially over time, with both Ucn- and CRF-treated animals eating significantly less than saline-injected controls earlier in the test period (4-5 hr) than did Ucn II-treated rats (6 hr).

Figure 10B:
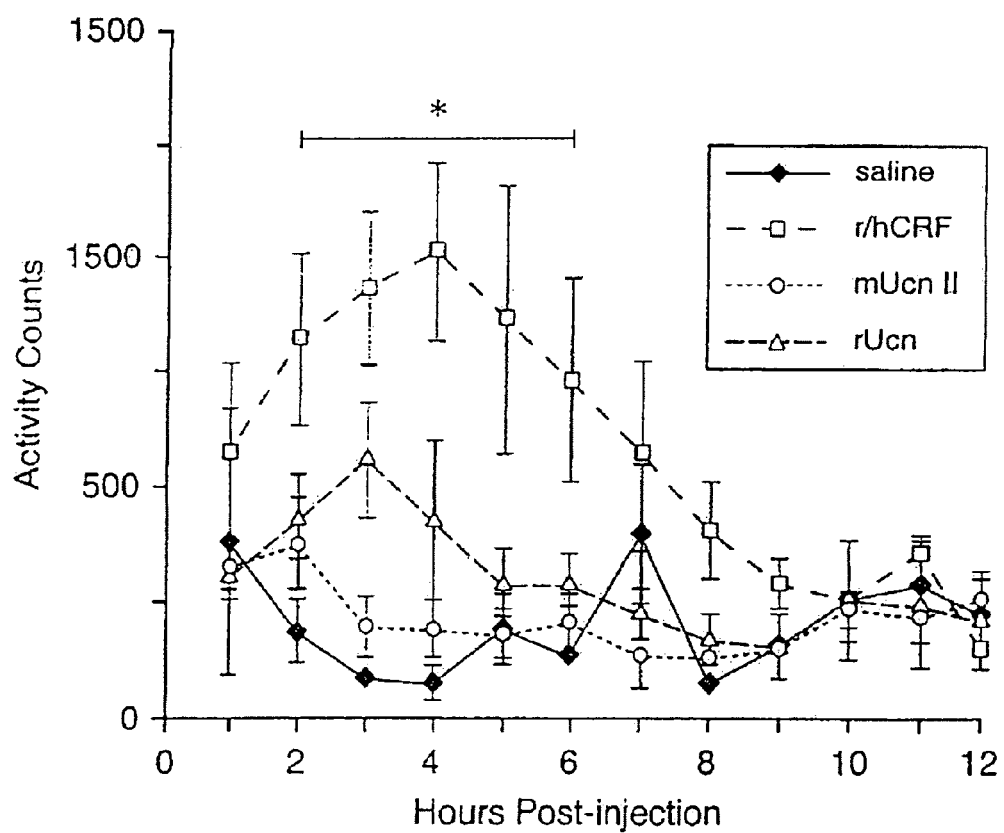

In these same subjects, gross motor activity and body temperature were monitored telemetrically (FIG. 10B). Analysis of activity data revealed a significant interaction between drug and time point [F (33,110)=1.94, p<0.006], with both main effects also achieving significance. Post-hoc comparisons revealed that animals that received CRF were significantly more active than vehicle-treated rats over the interval 2-6 hrs post-injection (p<0.001). Neither Ucn nor Ucn II treatment provoked reliable alterations in this measure at any post-injection time point. Core body temperature was also recorded, with each peptide provoking comparably mild (0.5-1° C.) and transient (2 hr) hypothermic responses (data not shown).

EXAMPLE 11

In Vitro Bioassay of HURP-Mediated Effects on Rat Anterior Pituitary Cells

Figure 11:
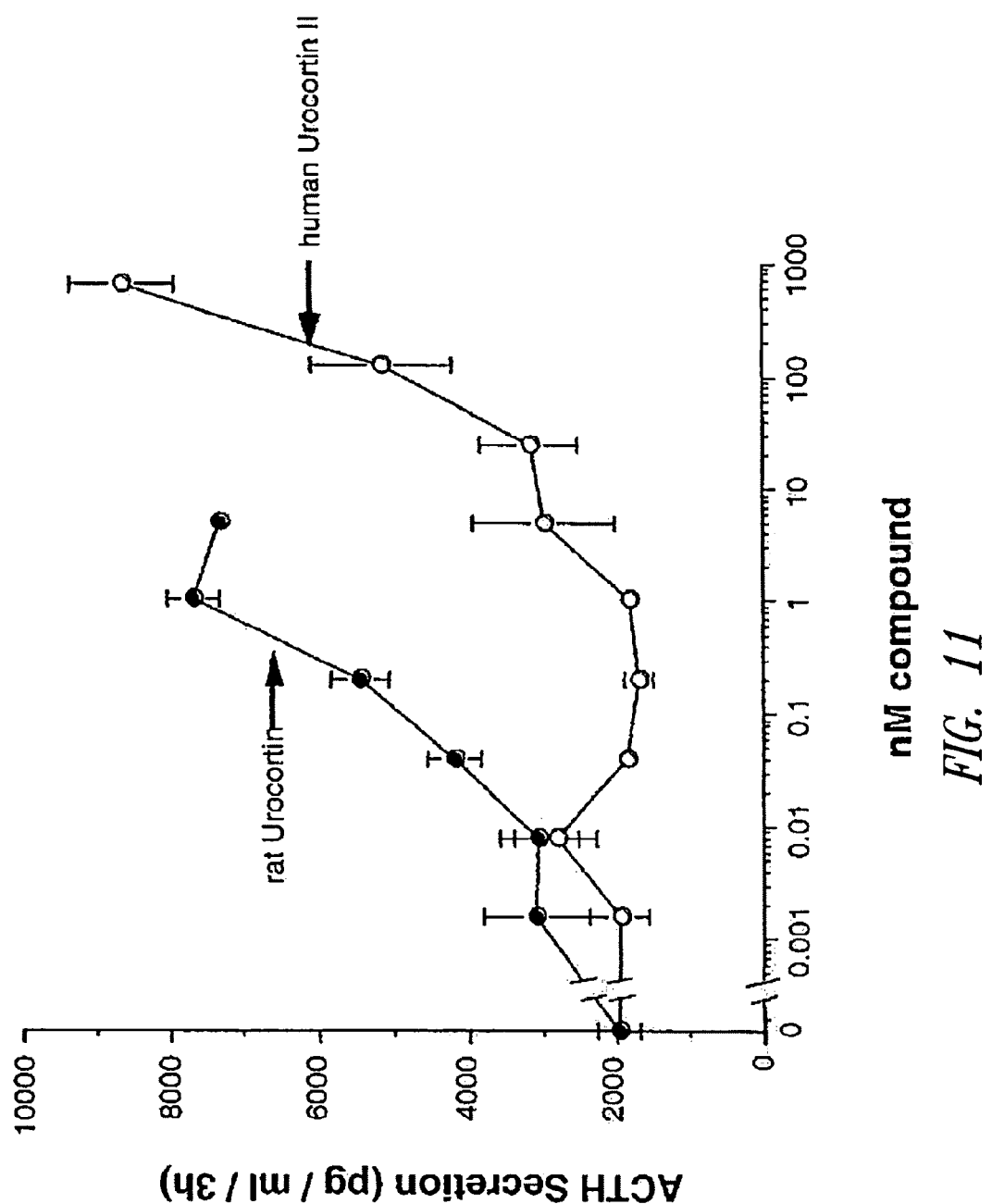
FIG. 11 shows stimulation of ACTH secretion from rat anterior pituitary cells by urocortin and human urocortin-related peptide. Rat anterior pituitary cells were established in culture and treated with either rat urocortin or human urocortin-related peptide. Secreted ACTH was measured using a kit (Nichols Institute Diagnostics).

For pituitary actions, ACTH secretion response to human urocortin-related peptide was measured in primary cultures of rat anterior pituitary cells as described (30). ACTH levels were determined using the ACTH immunoassay kit from Nichols Institute Diagnostics. The rat anterior pituitary cells were treated with either rat urocortin or human urocortin-related peptide and the level of secreted ACTH was measured, using a kit (Nichols Institute Diagnostics). The effects of urocortin and human urocortin-related peptide on ACTH secretion are shown in FIG. 11. The stimulation of ACTH secretion in anterior pituitary cells was found to be less sensitive to human urocortin-related peptide than to urocortin.

EXAMPLE 12

In Vitro Bioassay of the Effects of HURP on A7R5 Cells

Figure 12:
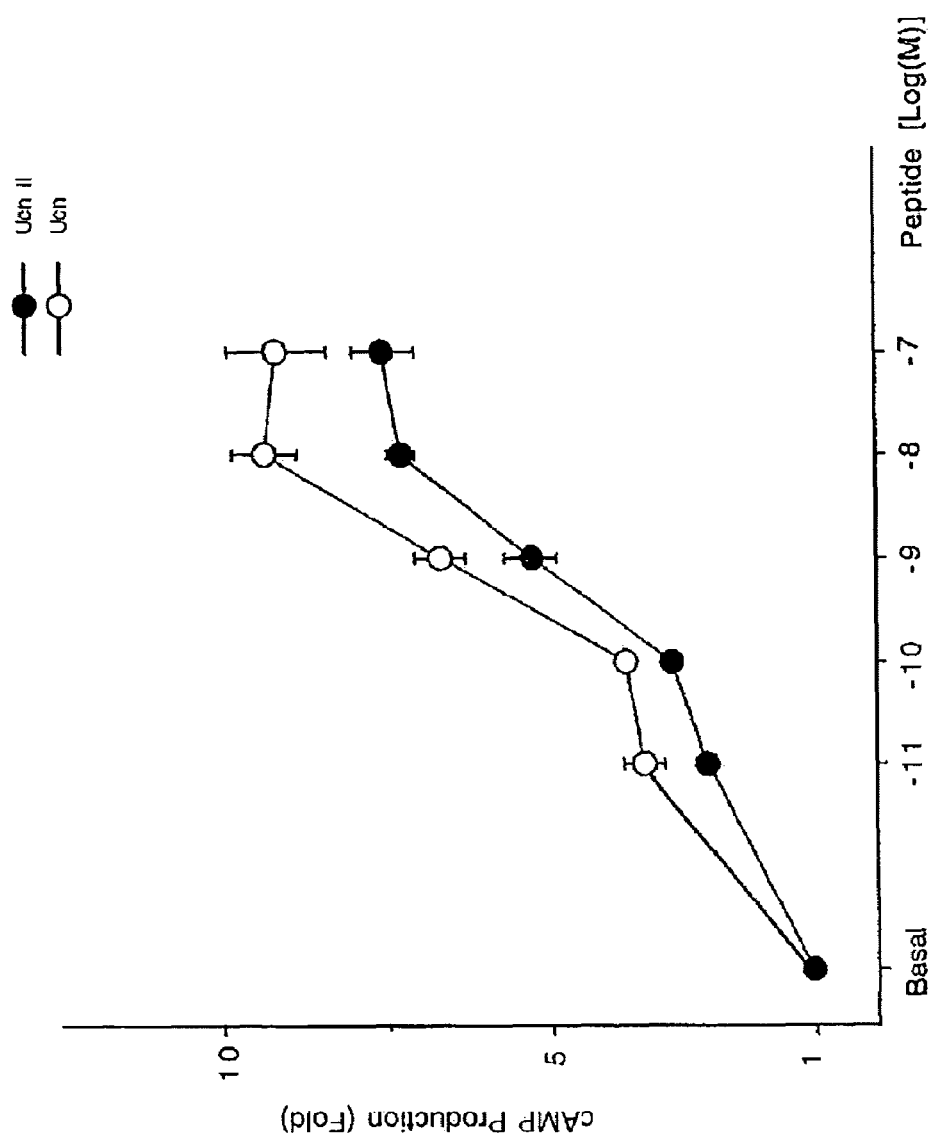
FIG. 12 shows the effect of human urocortin-related peptide on cAMP levels in A7R5 cells, which express native CRF-R2β. Dose-dependent effects of incubation with urocortin (open circle) or hURP (solid circle) for 30 minutes on cAMP production. cAMP was measured by RIA (Biochemical Technologies).

The effect of hURP on cAMP levels in A7R5 cells which express native CRF-R2β was determined. The A7R5 cell line was maintained in DMEM supplemented with 10% fetal bovine serum, 2 mM L-Glutamine, 100 μg/ml Streptomycin. Cells were seeded at 10,000 cells/cm2 and grown for six days. Serum starved cells were preincubated with 0.1 mM 3-isobutyl-l-methylxanthine in assay medium for 20 minutes and treated with the indicated concentrations of peptide for 30 minutes. cAMP levels were measured by RIA (Biochemical Technologies) and are shown in FIG. 12. Human urocortin-related peptide has similar effects on cAMP production as urocortin.

EXAMPLE 13

Effects of Human Urocortin-Related Peptide on Overall Activity

Figure 13:
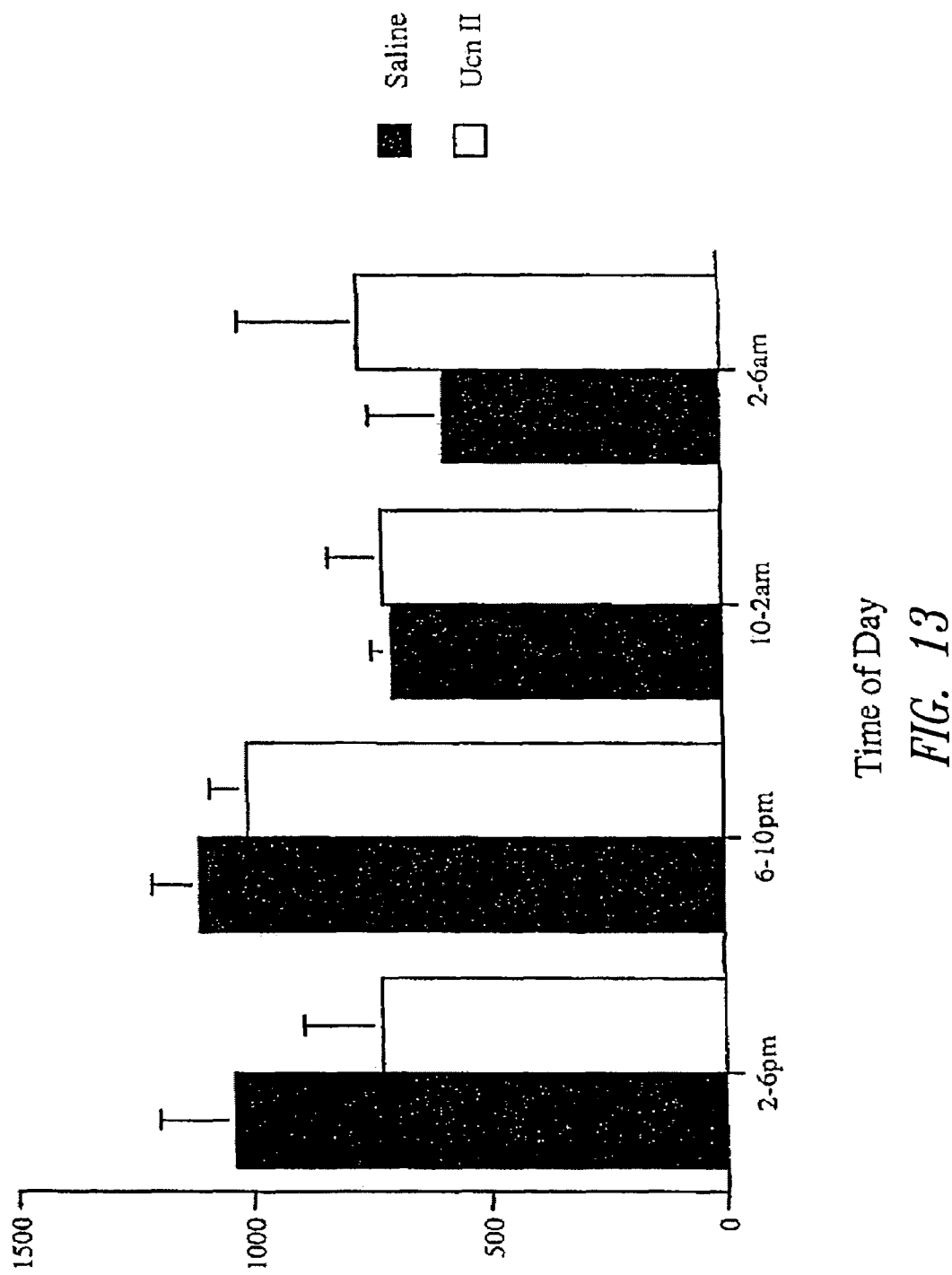
FIG. 13 shows the effects of human urocortin-related peptide (hURP) on gross motor activity in rats.

To determine if human urocortin-related peptide plays a role in the generation of stress response, the effect of human urocortin-related peptide on the gross motor activity of rats was examined. Cannulas were surgically into the right lateral ventricle while telemeters were implanted intraabdominally to allow for continuous monitoring of gross motor activity. The animals were allowed a post-surgical recovery period of seven days. During the time, the animals were handled daily to acclimatize the animals to the injection procedure. On the day of injection, baseline activity was for recorded for four hours. At 6:00 p.m., which was the onset of lights out, the animals received an injection of either 5 μl of saline or 5 μl of saline containing a total of 5 μg of human urocortin-related peptide. Activity counts were summated over a four hour time period. The results are summarized in FIG. 13. No significant difference in gross motor activity was seen in human urocortin-related peptide injected animals as compared to control animals.

EXAMPLE 14

Effects of Human Urocortin-Related Peptide on Body Temperature

Figure 14:
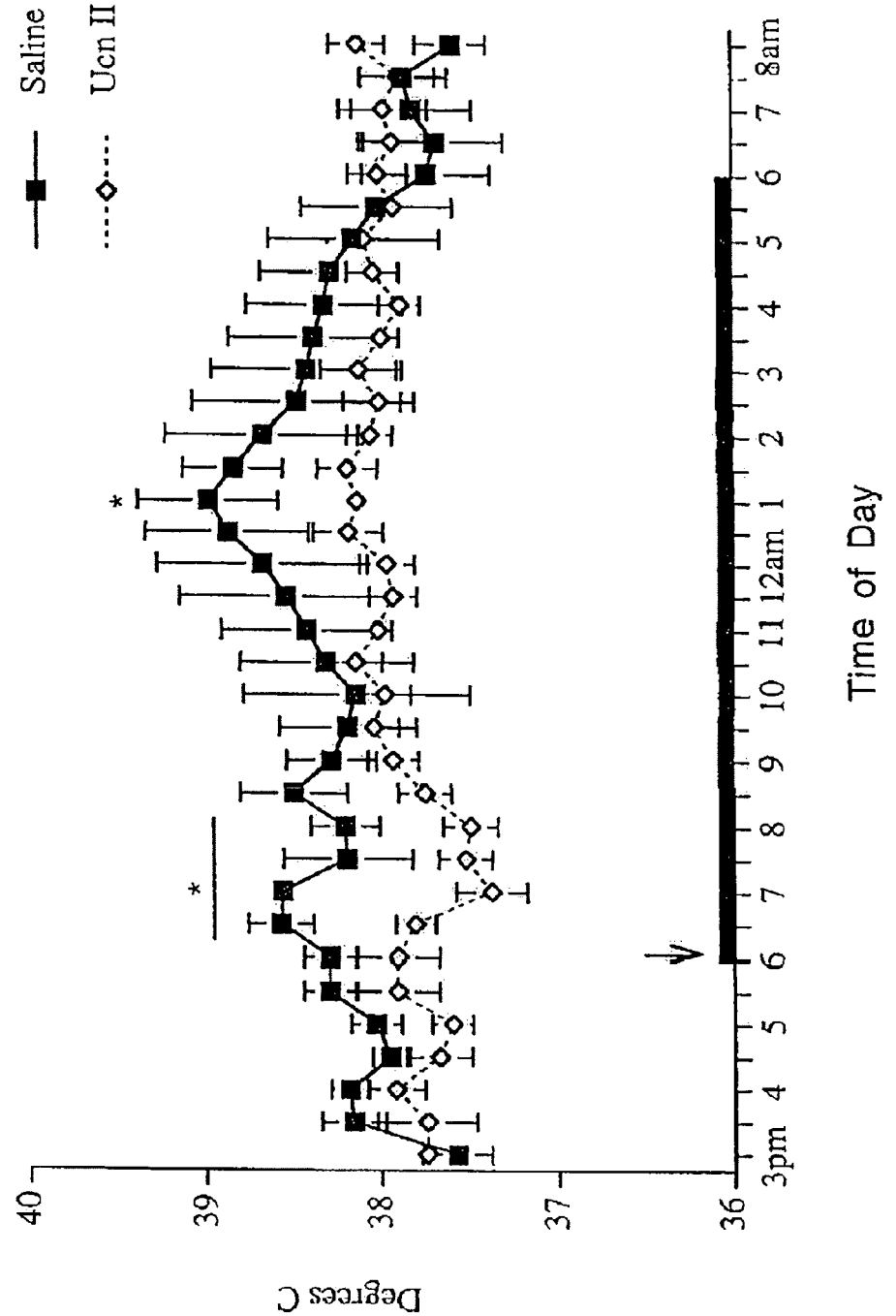
FIG. 14 shows the effects of intracerebroventricular injection of human urocortin-related peptide (URP) on body temperature in rats.

The effect of human urocortin-related peptide on the body temperature of rats was examined. Cannulas for injection of human urocortin-related peptide were surgically into the right lateral ventricle. Telemeters for the continuous unobtrusive analysis of body temperature were implanted intraabdominally. The animals were allowed a post-surgical recovery period of seven days. During the time, the animals were handled daily to acclimatize the animals to the injection procedure. On the day of injection, baseline temperature was for recorded for three hours. At 6:00 p.m. (the onset of lights out) the animals were injected with either 5 μl of saline or 5 μl of 1 μg/μl human urocortin-related peptide in saline. Body temperature was monitored every five minutes for twelve hours. As seen in FIG. 14, human urocortin-related peptide injected animals had lower body temperatures both immediately and at seven hours after injection.

EXAMPLE 15

Effects of Human Urocortin-Related Peptide on Appetite

The effect of human urocortin-related peptide on appetite was also examined in rats. Cannulas for injection of human urocortin-related peptide were surgically into the right lateral ventricle and the animals were allowed to recover for seven days. During the time, the animals were handled daily to acclimatize the animals to the injection procedure. On the day of injection, the animals were injected with either 5 μl of saline or 5 μl of 1 μg/μl human urocortin-related peptide in saline. The amount of food eaten by each animal was recorded every hour for six hours and at fourteen hours.

Figure 15A:
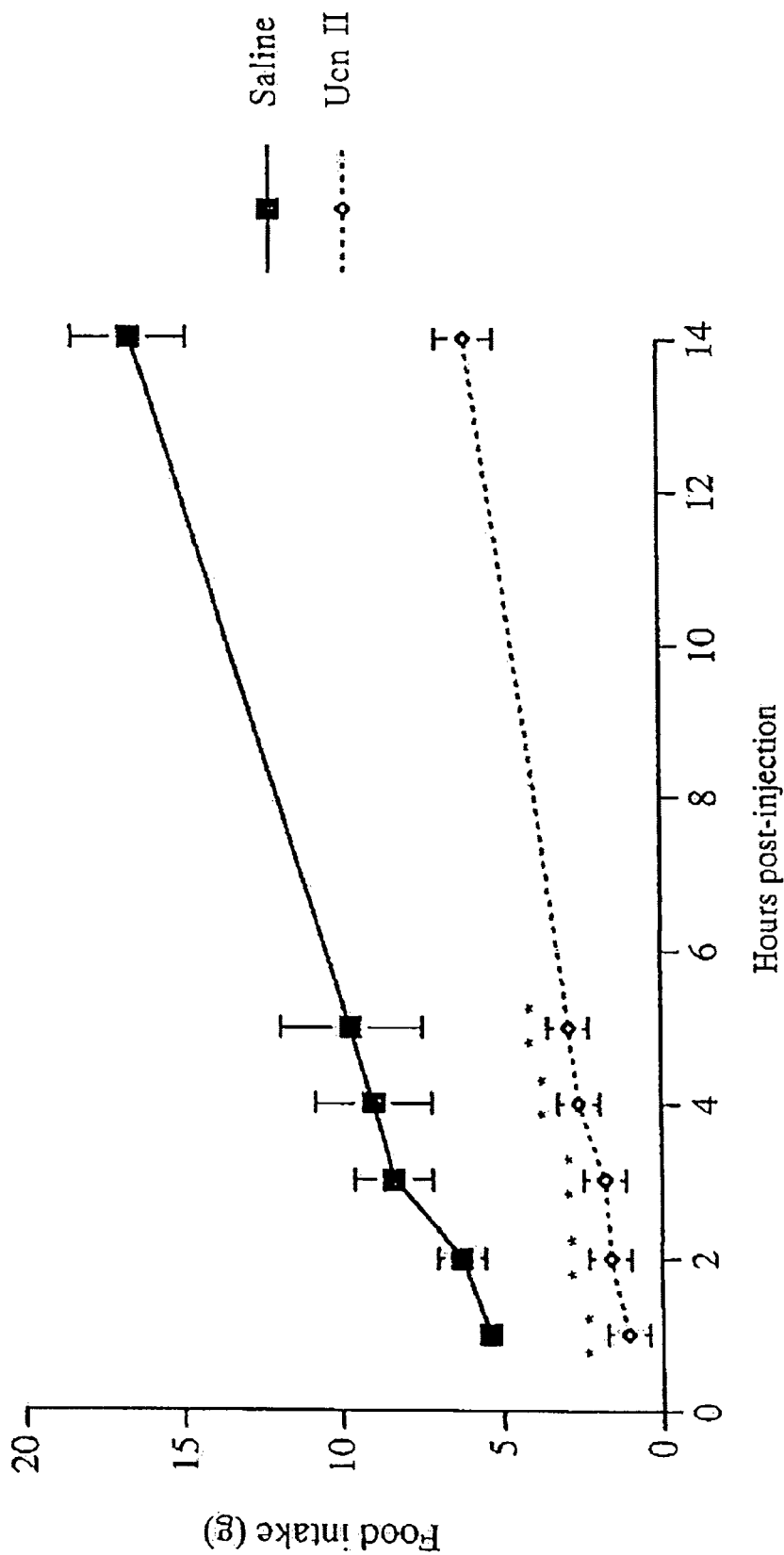
FIGS. 15A and 15B show the effects of intracerebroventricular injection of human urocortin-related peptide (hURP) on nocturnal food intake in rats.
Figure 15B:
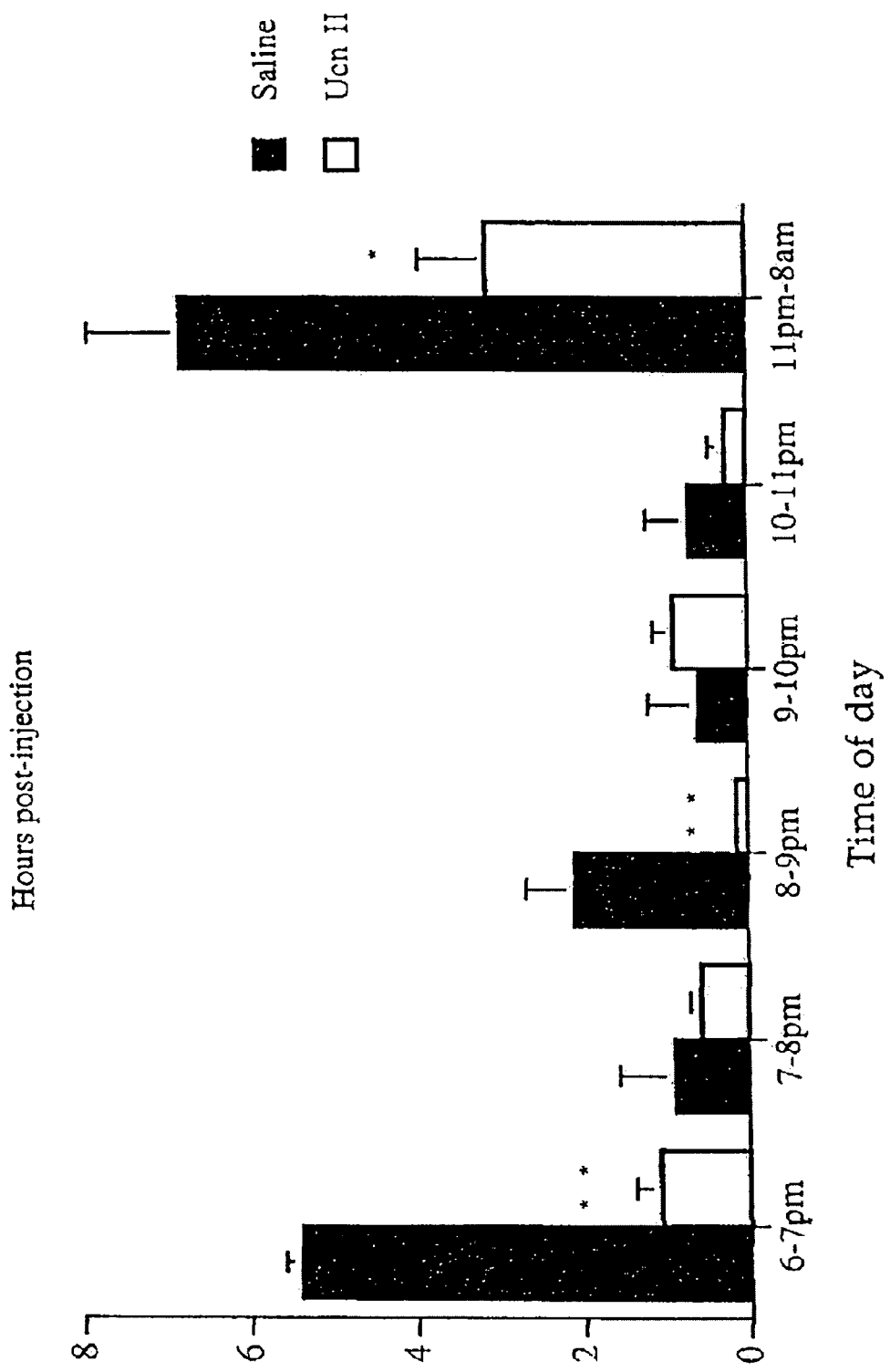
Figure 16:
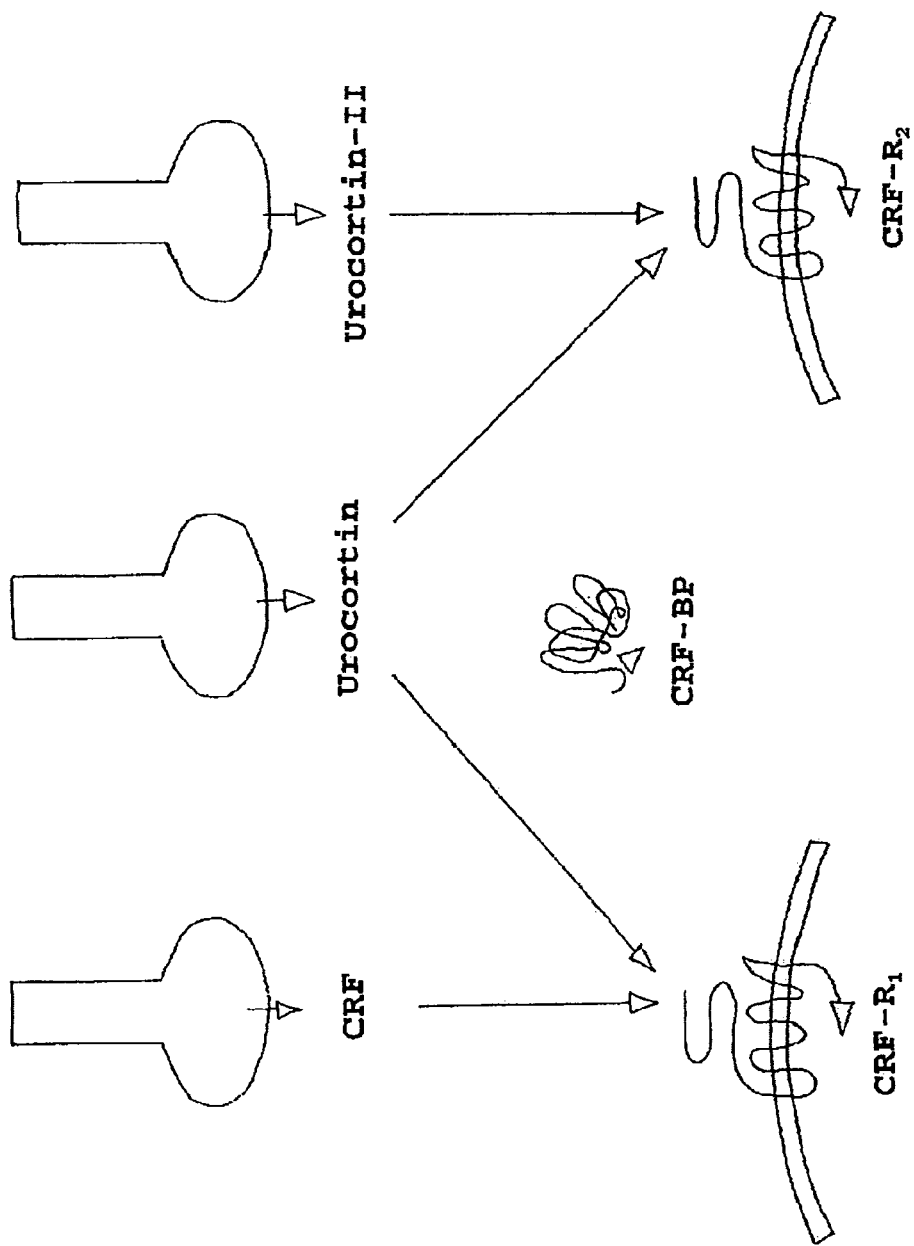
FIG. 16 show a model of how human urocortin-related peptide acts on CRF-R1 and CRF-R2. Human urocortin-related peptide binds with high affinity to CRF-R2 but not CRF-R1 while urocortin binds to both receptors. CRF binds with high affinity to CRF-R1 and not to CRF-R2.

The total food consumed over the course of the experiments is shown for each time period in FIG. 15A. Human urocortin-related peptide injected animals ate significantly less food than control animals. FIG. 15B summarizes the amount of food consumed during each time period. hURP treated animals especially ate less food during the first and third hours after injection as well as during the final eight hours of the experiment.

EXAMPLE 16

Useful Urocortin II and Human Urocortin-Related Peptide Modifications and Derivatives The urocortin II and human urocortin-related peptide disclosed herein most likely represent the prohormone forms of these proteins. It is contemplated that activation of the hormones will involve proteolytic processing and other type of modification to the proteins such as modification resulting in non-amidated forms of the proteins.

Previous studies with ligands for other CRE receptors have shown that a number of amino acid substitutions can be made to these ligands without losing the ability to bind to the receptors of the bioactivity of the ligands. A number of previous studies with urocortin have shown that one, two or even three substitutions are easily tolerated. In some instances modifications to urocortin resulted in protein with more desirable pharmacological properties. Since urocortin II and human urocortin-related peptide are small proteins, such modification can be most easily incorporated by peptide synthesis methods well known to those of skill in the art. These include solid phase techniques, partial solid phase, fragment condensation, and classical solution addition. These methods are especially preferred if nonstandard amino acids are to be incorporated into urocortin II or human urocortin-related peptide. Alternatively, if the modifications consist entirely of natural amino acids, recombinant DNA techniques can be used for mutagenesis and subsequent expression of modified urocortin II and human urocortin-related peptide.

Human urocortin-related peptide lacks a tyrosine residue. Since tyrosine residues are use for the radioiodination of proteins, one possible modification to human urocortin-related peptide would be substitute tyrosine for another amino acid in the protein. Previously, the addition of a sequence consisting of Tyr-Gly to the N-terminal end of urocortin was described. The resulting protein retains CRF receptor binding and bioactivity but would be useful in the radioiodination of the protein. Other N-terminal extensions of the protein of the instant invention may also be constructed for labeling and other purposes.

Deletion of the first seven to ten residues of urocortin was found to result in the formation of effective urocortin antagonists. These proteins were capable of binding to CRF receptors but did not significantly stimulate or activate the receptors. It is expected that deletion of up to five amino acids from urocortin II or human urocortin-related peptide would result in effective antagonists as well. It may also be possible to create antagonists from other urocortin II and human urocortin-related peptide fragments. These antagonists can be effective in elevating levels of the endogenous peptides which are normally cleared by CRF-binding protein. By associating with the CRF-binding protein and blocking CRF, urocortin, urocortin II and human urocortin-related peptide binding to the same protein, the effective in vivo concentrations of endogenous CRF, Ucn and Ucn II are increased. Such antagonists can, be coadministered with other agonists, or antagonists of CRF, Ucn, Ucn II or URP for enhancement of the effects thereof.

Extensive analysis of other CRF receptor binding proteins has shown that substitution of normal amino acids with D-isomer amino acids or cyclizing amino acids results in increased affinity for CRF-receptors. In particular, an especially useful substitution is replacement of the isoleucine residue corresponding to position 9 of SEQ ID NO: 3 or SEQ ID NO: 11 with a "D-form" isomeric amino acid, preferably D-isoleucine, D-phenylalanine, and D-Leucine. Likewise, a glutamic acid residue corresponding to position 17 of SEQ ID NO: 3 or SEQ ID NO: 11 can be replaced with D-glutamic acid. Cyclizing amino acids can be formed by chemical bonds between the side chains of two or more residues. For example, adjacent glutamic acid and lysine residues can react to form an amide bond producing a lactam ring. Substitution with nonstandard amino acids such as $C_{60}$-methylated leucine, $C_{\alpha}$-methylated alanine, N-im-benzylhistidine, 4-hydroxyproline, 5-hydroxylysine, 3-methylhistidine, homoserine, and ornithine may also be used to form agonists or antagonists of human urocortin-related peptide.

The modifications to urocortin II and human urocortin-related peptide disclosed herein are intended to be illustrative of possible modification that may be performed and are not intended to limit the invention in any way.

Discussion

Genome-wide homology searching was used to identify new members of the CRF family of neuropeptides. One of the new ligands, Ucn II, binds selectively to CRF-R2, is expressed in discrete areas of the rat CNS, and activates central neurons involved in the processing of visceral sensory information, and in modulating autonomic outflow. Further, Ucn II inhibits food intake, without any effect on gross motor activity.

In addition to a murine peptide that exhibits structural, binding, activity and expression characteristics expected of a CRF family member, a human URP (based on a publicly available EST sequence) was identified which is 80% identical to the mouse sequence at the nucleotide level. However, an important difference evident in the human peptide is the absence of any obvious proteolytic cleavage site that would provide for C-terminal processing of a human homologue. It remains to be determined whether and how any homologous human peptide may be generated from this protein. Nevertheless, whereas Ucn is bound with high affinity by, and signals potently through, both CRF-R1 and CRF-R2 (14-16). Mouse Ucn II and human URP exhibit a high degree of CRF-R2 selectivity in these measures, and will doubtless be of value in dissociating functions mediated by the two receptor types. FIG. 16 shows a model of how urocortin II acts on CRF-R1 and CRF-R2. Ucn II binds with high affinity to CRF-R2 and not CRF-R1. Urocortin binds to both receptors while CRF binds with high affinity to CRF-R1 but not to CRF-R2.

Ucn II mRNA displays a limited subcortical distribution in rodent brain that is unique, though ostensibly overlapping in part with those of CRF (paraventricular nucleus; e.g., ref. 31) and Ucn (brainstem and spinal motor nuclei; e.g., ref. 18). Of particular interest is the fact that the transcript is expressed in cell groups involved in stress-related physiologic and behavioral functions (see ref. 13). This includes the locus coeruleus, which issues widespread projections to the cortical mantle and has been implicated in generating levels of arousal and anxiety (e.g., 3:2), the paraventricular nucleus, which houses multiple relevant neurosecretory neuron populations and projects within the CNS to modulate sensory and motor traffic in central autonomic circuitry (e.g., 33), and the arcuate nucleus, which has been identified as a pivotal component of an extended system subserving the regulation of food intake and energy balance (e.g., 34). Although anatomical and functional data to define the new peptide's place in such contexts are as yet lacking, the central Ucn II system holds potential for participating in stress-related functions long implicated as the province of the broader central CRF network. This contrasts with Ucn, whose dominant seat of cellular expression in brain, the Edinger-Westphal nucleus, shows very limited capacities in this regard, largely by virtue of a paucity of documented projections to the forebrain (16, 18).

In view of its binding characteristics and activity, the failure of the pattern of cellular activation elicited by central Ucn II to closely mimic the CRF-R2 distribution was unexpected. A recent study comparing the distribution of Fos expression induced by icv CRF or UCN documented activation patterns coarsely consistent with the binding affinities of these peptides for CRF-Rs encoded by the two known genes (35). That is, CRF at doses similar to those employed here activated sites of CRF-R1 expression in a highly preferential manner, while UCN provoked Fos induction mainly in subsets of cell groups that express each receptor. In addition, however, both peptides recruited the very same set of central autonomic structures that were seen here to be the dominant seats of Ucn II-induced activational responses in the rat brain. This is significant in that elements of the central autonomic system are among the best documented sites at which CRF-like peptides can act to elicit stress-related autonomic and behavioral responses. These findings would suggest that type 2, as well as type 1, receptor activation is capable of engaging this system, though the basis for this is unclear. Among the nodal points in the central autonomic network, only the parabrachial nucleus (R1) and the NTS (R2) have been identified as sites of CRF-R expression (27, 28, 35) and it remains to be determined whether receptor-mediated activation of either or both of these is sufficient to enlist the system as a whole. It is important to note that systemic injections of synthetic Ucn II failed to elicit comparably powerful activational responses within central autonomic cell groups over the same range of doses that were used for icv injection studies. This is an important control, as activation of peripheral CRF-R2 can yield a marked and persistent reduction in blood pressure (16, 17), and salient hypotensive challenges are capable of activating the very same central autonomic structures as are responsive to central Ucn II administration (36, 37).

The initial characterization of the effects of icv Ucn II on food intake and activity complements recent efforts to tease apart the roles of individual CRF-Rs in stress-related behaviors. For example, while mice bearing null mutations of either receptor display normal basal food intake, CRF-R1-deficient animals have been shown to be refractory to the anorexic effects of UCN during the period immediately following injection, but not at later time points, while the converse is true of CRF-R2 mutant mice (11, 38, 39). This has been taken as suggesting that the early and later phase of Ucn-mediated feeding suppression may be CRF-R1-and CRF-R2-mediated events, respectively. Using a different paradigm (nighttime free-feeding rather than deprivation-induced refeeding) provided data supportive of such a parsing, as the R2-specific ligand did not reliably suppress food intake at the early time points, but did so beyond 6 hrs post-injection.

Measures of motor activity also supported a dissociation of CRF-R involvement in this parameter. In line with recent evidence in knockout mice suggesting locomotor activation to be a CRF-R1-mediated event (40), it was found that the R1-selective agonist, CRF, significantly increased gross motor activity, while UCN II administration did not. Interestingly, treatment with UCN, which is bound with high affinity by both receptors, resulted in a non significant trend toward increased activity, with values being reliably lower than those seen in response to CRF. This is coarsely consistent with a growing body of evidence to support a functional antagonism between the two known receptor types. Whereas CRF-R1-deficient mice show reduced endocrine and anxiety-like responses to stress (41), CRF-R2 mutant lines display increases in these parameters (11, 39, 42) suggesting that basal activation of CRF-R2 may play a role in opposing CRF-R1-driven stress responses.

The identification of an endogenous CRF-R2-selective ligand will allow for more detailed analysis of the roles of individual CRF-related signaling molecules in stress-related physiologic and behavioral functions. Central expression of Ucn II mRNA identified cell groups that respond to central administration of the peptide; and confirmed behavioral responses that are consistent with previously hypothesized consequences of CRF-R2 activation.

Further insight into the place of this peptide in stress biology will require delineation of the central projections of Ucn II containing cells, and identification of the factors and circumstances that regulate gene expression and peptide release.

The following references were cited herein:

1. Vale, W., Spiess, J., Rivier, C. & Rivier, J. (1981) *Science* 213, 1394-7.
2. Menzaghi, F., Heinrichs, S. C:, Pich, E. M., Weiss, R. & Koob, G. F. (1993) *Ann. N.Y. Acad. Sci.* 697, 142-154.
3. Sawchenko, P. E., Imaki, T., Potter, E., Kovacs, K., Imaki, J. & Vale, W. (1993) *Ciba Foundation Symposium* 172, 5-21.
4. Rivier, C. and Vale W. (1983) *Nature*, 1983. 305, 325-327.
5. Rivier, J., C. Rivier, and Vale W. (1984) in *European Peptide Symposium*, Djuronaset. Sweden. p. 104.
6. Chen, R.; et al. (1993) *Proc. Natl. Acad. Sci. USA*, 1993. 90, 8967-8971.
7. Perrin, M. H., et al. (1995) *Proc. Natl. Acad. Sci. USA*, 92, 2969-2973.
8. Potter, E., et al. (1994) in *76th Annual Meeting of The Endocrine Society*, Anaheim, Calif., p. 217.
9. Lovenberg, T. W. et al. (1995) *Endocrinology*, 136, 3351-3355.
10. Rohde, E., et al. (1996) *Biochem Pharmacol*, 52(6), 829-33.
11. Bale, T. L., et al. (1999) *Nat. Genet.*, 24(4), p. 410-414.
12. Herkenham, M. (1987) *Neuroscience* 23, 1-38.
13. Bittencourt, et al. (2000) *J. Neurosci.* 20, 1142-56.
14. Behan, et al. (1996) *Molec. Psychiatry* 1, 265-277.
15. Turnbull, et al. (1997) *Proc. Soc. Exp. Biol. Med.* 215, 1-10.
16. Vaughan, et al. (1995) *Nature* 378, 287-92.
17. Spina, et al. (1996) *Science* 273, 1561-4.
18. Bittencourt, et al. (1999) *J. Comp. Neurol.* 415, 285-312.
19. Eddy, S. R. (1996) *Curr. Opinion Struct. Biol.* 6, 361-365.
20. Brunner, et al. (2000) *Chromosome Res.* 8, 465-476.
21. Miranda, et al. (1994) *J. Med. Chem.* 37, 1450-9. 94238641
22. Miller, C. & Rivier, J. (1996) *Biopolymers* 40, 265-317.
23. Simmons, et al. (1989) *J. Histotechnol.* 12,168-181.
24. Sawchenko, et al. (1990) *Meth. Neurosci.* 3, 247-260.
25. Sawchenko, P. E. (1983) *J. Auton. Nerv. Syst.* 9, 13-26.
26. Saper, C. B. (1995) in *The Rat Nervous System* (2nd edition), ed. G. Paxinos, (Academic Press, San Diego) pp. 107-128.
27. Van Pett; et al. (2000) *J. Comp. Neurol.* 428, 191-212.
28. Chalmers, et al. (1995) *J. Neurosci.* 15, 6340-6350.
29. Gray, P. C., et al., (2000) *J. Biol. Chem.*, 275(5): p. 3206-3212.
30. Vale, W., et al., (1983) *Methods in Enzymology: Neuroendocrine Peptides*, P. M. Conn, Editor. Academic Press: New York. p. 565-577. Biomedical Technologies Inc.
31. Swanson, et al. (1983) *Neuroendocrinology* 36, 165-186.
32. Bremner, et al. 1996 *Synapse* 23, 28-38.
33. Swanson, et al. (1983) *Ann. Rev. Neurosci.* 6, 269-324.
34. Elmquist, et al. 1998 *Nature Neurosci.* 1, 445-450.
35. Potter, et al. (1994) *Proc. Natl. Acad. Sci. USA*, 91, 8777-8781.

36. Li, et al. (1994) Expression of Fos-like protein in brain following sustained hypertension and hypotension in conscious rabbits. *Neuroscience* 61, 613-634.

37. Chan, et al. (1994) *J. Comp. Neurol.* 348, 433-460.

38. Bradbury, et al. (2000) *Endocrinology* 141, 2715-2724.

39. Coste, et al. (2000) *Nature Genet.* 24, 403-409.

40. Contarino, et al. (2000) *Endocrinology* 141, 2698-2702.

41. Smith, et al. (1998) *Neuron* 20,1093-1102

42. Kishimoto, et al. (2000) *Nature Genet.* 24, 415-419.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A pharmaceutical composition comprising a human urocortin-related peptide having the amino acid sequence shown in SEQ ID NO:3 and a pharmaceutically acceptable carrier.

2. The pharmaceutical composition of claim 1, wherein said peptide is amidated at the C-terminus.

3. A pharmaceutical composition comprising a human urocortin-related peptide having the amino acid sequence shown in SEQ ID NO:4.

4. The pharmaceutical composition of claim 3, wherein said peptide is amidated at the C-terminus.

* * * * *

UNITED STATES PATENT AND TRADEMARK OFFICE
CERTIFICATE OF CORRECTION

PATENT NO. : 7,638,607 B2 Page 1 of 1
APPLICATION NO. : 11/784317
DATED : December 29, 2009
INVENTOR(S) : Wylie Walker Vale, Jr. et al.

It is certified that error appears in the above-identified patent and that said Letters Patent is hereby corrected as shown below:

Title page Item 57, Line 3
"mouse CDNA was isolated from whole brain poly (A+) RNA" should read --mouse cDNA was isolated from whole brain poly (A+) RNA--

Signed and Sealed this

Twenty-second Day of June, 2010

David J. Kappos
*Director of the United States Patent and Trademark Office*